United States Patent
Jiang et al.

(10) Patent No.: US 7,262,174 B2
(45) Date of Patent: Aug. 28, 2007

(54) TREATMENT FOR WOUNDS

(75) Inventors: Xu-Rong Jiang, Mountain View, CA (US); Choy-Pik Chiu, Cupertino, CA (US); Calvin B. Harley, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 367 days.

(21) Appl. No.: 10/143,536

(22) Filed: May 9, 2002

(65) Prior Publication Data

US 2004/0147465 A1 Jul. 29, 2004

Related U.S. Application Data

(60) Provisional application No. 60/289,903, filed on May 9, 2001.

(51) Int. Cl.
*A61K 48/00* (2006.01)
(52) U.S. Cl. ........................ 514/44; 424/93.1
(58) Field of Classification Search ............... 424/93.1, 424/93.2, 93.21, 93.3; 514/2, 12, 44; 536/23.1; 435/325
See application file for complete search history.

(56) References Cited

U.S. PATENT DOCUMENTS

| | | | |
|---|---|---|---|
| 4,016,036 A | 4/1977 | Green et al. .................. | 195/1.8 |
| 4,304,866 A | 12/1981 | Green et al. ................. | 435/240 |
| 4,745,098 A | 5/1988 | Michaeli ........................ | 514/2 |
| 4,837,024 A | 6/1989 | Michaeli ...................... | 424/446 |
| 5,556,620 A | 9/1996 | Ralph et al. ................. | 424/85.1 |
| 5,561,107 A | 10/1996 | Jaynes et al. .................. | 514/12 |
| 5,580,781 A | 12/1996 | Naughton et al. ........... | 435/240 |
| 5,583,016 A | 12/1996 | Villeponteau et al. ..... | 435/91.3 |
| 5,641,670 A | 6/1997 | Treco et al. | |
| 5,698,436 A | 12/1997 | Morgan et al. .......... | 435/240.2 |
| 5,718,897 A | 2/1998 | Herman .................... | 424/94.67 |
| 5,720,981 A | 2/1998 | Eisinger ..................... | 424/572 |
| 5,733,761 A | 3/1998 | Treco et al. | |
| 5,824,647 A | 10/1998 | Postlethwaite et al. ....... | 514/13 |
| 5,861,153 A | 1/1999 | Schmidt et al. ............ | 424/93.7 |
| 5,965,530 A | 10/1999 | Pierce et al. ................... | 514/12 |
| 5,980,888 A | 11/1999 | Dimoudis et al. ......... | 424/93.7 |
| 5,997,863 A | 12/1999 | Zimmermann et al. .... | 424/94.5 |
| 6,025,150 A | 2/2000 | Livant .......................... | 435/29 |
| 6,077,602 A | 6/2000 | Liestman et al. ........... | 428/327 |
| 6,110,208 A | 8/2000 | Soranzo et al. ............... | 623/15 |
| 6,166,178 A | 12/2000 | Cech et al. .................. | 530/324 |
| 6,191,110 B1 | 2/2001 | Jaynes et al. .................. | 514/12 |
| 6,261,556 B1 | 7/2001 | Weinrich et al. ........... | 424/94.5 |
| 6,261,836 B1 | 7/2001 | Cech et al. .................. | 435/325 |
| 6,617,110 B1 | 9/2003 | Cech et al. | |

FOREIGN PATENT DOCUMENTS

| | | |
|---|---|---|
| WO | WO97/08295 | 3/1997 |
| WO | WO97/23602 | 7/1997 |
| WO | WO99/27113 | 6/1999 |
| WO | WO99/47644 | 9/1999 |
| WO | WO99/54435 | 10/1999 |
| WO | WO 00/31238 | 6/2000 |
| WO | WO 00/47148 | 8/2000 |

OTHER PUBLICATIONS

Bodnar, et al., Extension of life-span by introduction of telomerase into normal human cells, Science 279:349 (1998).
Campisi, et al., The role of cellular senescence in skin aging, J Investig Dermatol Symp Proc. 3:1 (1998).
Deveci, M., Telomeres and telomerase and their possible future in plastic surgery, Plast. Reconstr. Surg. 104:1588 (1999).
Dickson, et al., Human keratinocytes that express hTERT and also bypass a p16(INK4a)-enforced mechanism that limits life span become immortal yet retain normal growth and differentiation charachteristics, Mol. Cell. Biol. 20:1436 (2000).
Driscoll, et al., Telomerase in alveolar epithelial development and repair, Am J. Physiol. Lung. Cell. Mol. Physiol. 279:L1191 (2000).
Farwell, et al., Genetic and epigenetic changes in human epithelial cells immortalized by telomerase, Am. J. Pathol. 156:1537 (2000).
Fujimoto, et al., Expression of telomerase components in oral keratinocytes and squamous cell carcinomas, Oral. Oncol. 37:132 (2001).
Funk, et al., Telomerase expression restores dermal integrity to in vitro-aged fibroblasts in a reconstituted skin model, Exp. Cell Res. 258:270 (2000).
Gonzalez-Suarez, et al., Increased epidermal tumors and increased skin wound healing in transgenic mice overexpressing the catalytic subunit of telomerase, mTERT, in basal keratinocytes, EMBO J 20:2619 (2001).
Harle-Bachor, et al., Telomerase activity in the regenerative basal layer of the epidermis in human skin and in immortal and carcinoma-derived skin keratinocytes, Proc. Natl. Acad. Sci. USA 93:6476 (1996).
Holmberg, et al., Ester synthesis with dicyclohexylcarbodiimide improved by acid catalysts, Acta Chemica Scandinavica B 33:410 (1979).
Jiang, et al., Telomerase expression in human somatic cells does not induce changes associated with a transformed phenotype, Nat. Genet. 21:111 (1999).
Kang, et al., Replicative senescence of normal human oral keratinocytes is associated with the loss of telomerase activity without shortening of telomeres, Cell Growth Differ. 9:85 (1998).

*Primary Examiner*—Jon Eric Angell

(57) ABSTRACT

It has been discovered that increasing telomerase activity in cells surrounding a wound has a variety of effects that enhance wound healing. Replication capacity is enhanced, and the mobility of the epithelial cells can be increased by 3-fold or more. Some aspects of the invention relate to agents that increase telomerase activity in cells at the site of the wound, promoting cells to move to the site and restore an epithelial layer and the underlying stratum. Other aspects of the invention relate to compositions comprising epithelial cells in which telomerase activity has been increased, useful as grafts for the treatment of wounds.

16 Claims, 23 Drawing Sheets

OTHER PUBLICATIONS

Kiyono, et al., Both Rb/p16$^{INK4a}$ inactivation and telomerase activity are required to immortalize human epithelial cells, Nature 396:84 (1998).

LaFrance, et al., Novel living skin replacement biotherapy approach for wounded skin tissues, Tissue Eng 5:153 (1999).

Li, et al., Identification and isolation of candidate human keratinocyte stem cells based on cell surface phenotype, Proc Natl Acad Sci USA 95:3902 (1998).

Martin, Wound healing—aiming for perfect skin regeneration, Science 276:75 (1997).

Mattson, et al., Emerging roles for telomerase in neuronal development and apoptosis, J. Neurosci Res 63:1 (2001).

Matsui, et al., Influence of aging and cell senescence on telomerase activity in keratinocytes, J. Dermatol. Sci. 22:80 (2000).

Mendez, et al., Fibroblasts cultured from venous ulcers display cellular characteristics of senescence, J. Vasc. Surg. 28:876 (1998).

Morales, et al., Lack of cancer-associated changes in human fibroblasts after immortalization with telomerase, Nature Genet. 21:115 (1999).

Nakamura, et al., Telomerase Catalytic Subunit Homologs from Fission Yeast and Human, Science 277:955 (1997).

Ogoshi, et al., In situ hybridization analysis of the expression of human telomerase RNA in normal and pathologic conditions of the skin, J. Invest. Dermatol. 110:818 (1998).

Osanai, et al., Transcient increase in telomerase activity of proliferating fibroblasts and endothelial cells in granulation tissue of the human skin, Wound Repair Regen. 10:59 (2002).

Ramirez, et al., Telomerase activity concentrates in the mitotically active segments of human hair follicles, J. Invest. Dermatol. 108:113 (1997).

Ramirez, et al., Progressive Increase in Telomerase Activity From Benign Melanocytic Conditions to Malignant Melanoma, Neoplasia 1:00 (1999).

Ramirez, et al., Putative telomere-indepentant mechanisms of replicative aging reflect inadequate growth conditions, Genes & Dev. 15:398 (2001).

Rambatla, et al., In vitro differentiation capacity of telomerase immortalized human RPE cells, invest Ophthalmol. Vis. Sci. 43:1622 (2002).

Rudolph, et al., Longevity, stress response, and cancer in aging telomerase-deficient mice, Cell 96:701 (1999).

Taylor, et al., Detection of Telomerase Activtion in Malignant and Nonmalignant Skin Conditions, J. Invest. Dermatol. 106:759 (1996).

Ueda, et al., Evidence for UV-associated Activation of Telomerase in Human Skin, Cancer Research 57:370 (1999).

Voigt, et al., Cultured epidermal keratinocytes on a microspherical transport system are feasible to reconstitute the epidermis in full-thickness wounds, Tissue Eng. 5:563 (1999).

Wang, et al., Risky immortalization by telomerase, Nature 405:755 (2000).

Yang, et al., Human endothelial cell life-extension by telomerase expression, J. Biol. Chem. 274:26141 (1999).

Yang, et al., Telomerized human microvasculature is functional in vivo, Nat. Biotechnol. 19:219 (2001).

Zhao, P., et al., Telomerase activity in radiation-induced chronic human skin ulcers, J. Environ. Pathol. Toxicol. Oncol. 18:17 (1999).

Zhou, et al., Expression of telomerase reverse transcriptase in radiation-induced chronic human skin ulcer, J. Environ. Pathol. Toxicol. Oncol. 21:67 (2002).

a b

Effect of hTERT retrovirus on wound closure

Effect of hTERT adenovirus on wound closure

Effect of Mitomycin c on cell proliferation day 0 day 3 day 10

SEQUENCE LISTING

<160> NUMBER OF SEQ ID NOS: 2

<210> SEQ ID NO 1
<211> LENGTH: 4015
<212> TYPE: DNA
<213> ORGANISM: Homo sapiens
<220> FEATURE:
<221> NAME/KEY: CDS
<222> LOCATION: (56)..(3454)
<223> OTHER INFORMATION:

<400> SEQUENCE: 1

```
gcagcgctgc gtcctgctgc gcacgtggga agccctggcc ccggccaccc ccgcg atg        58
                                                              Met
                                                              1 ccg cgc gct ccc cgc tgc cga gcc gtg cgc tcc ctg ctg cgc agc cac        106
Pro Arg Ala Pro Arg Cys Arg Ala Val Arg Ser Leu Leu Arg Ser His
        5                  10                  15 tac cgc gag gtg ctg ccg ctg gcc acg ttc gtg cgg cgc ctg ggg ccc        154
Tyr Arg Glu Val Leu Pro Leu Ala Thr Phe Val Arg Arg Leu Gly Pro
 20                  25                  30 cag ggc tgg cgg ctg gtg cag cgc ggg gac ccg gcg gct ttc cgc gcg        202
Gln Gly Trp Arg Leu Val Gln Arg Gly Asp Pro Ala Ala Phe Arg Ala
         35                  40                  45 ctg gtg gcc cag tgc ctg gtg tgc gtg ccc tgg gac gca cgg ccg ccc        250
Leu Val Ala Gln Cys Leu Val Cys Val Pro Trp Asp Ala Arg Pro Pro
 50                  55                  60                  65 ccc gcc gcc ccc tcc ttc cgc cag gtg tcc tgc ctg aag gag ctg gtg        298
```

```
                Pro Ala Ala Pro Ser Phe Arg Gln Val Ser Cys Leu Lys Glu Leu Val
                                70                  75                  80 gcc cga gtg ctg cag agg ctg tgc gag cgc ggc gcg aag aac gtg ctg            346
Ala Arg Val Leu Gln Arg Leu Cys Glu Arg Gly Ala Lys Asn Val Leu
            85                  90                  95 gcc ttc ggc ttc gcg ctg ctg gac ggg gcc cgc ggg ggc ccc ccc gag            394
Ala Phe Gly Phe Ala Leu Leu Asp Gly Ala Arg Gly Gly Pro Pro Glu
                100                 105                 110 gcc ttc acc acc agc gtg cgc agc tac ctg ccc aac acg gtg acc gac            442
Ala Phe Thr Thr Ser Val Arg Ser Tyr Leu Pro Asn Thr Val Thr Asp
            115                 120                 125 gca ctg cgg ggg agc ggg gcg tgg ggg ctg ctg cgc cgc gtg ggc                490
Ala Leu Arg Gly Ser Gly Ala Trp Gly Leu Leu Arg Arg Val Gly
130                 135                 140                 145 gac gac gtg ctg gtt cac ctg ctg gca cgc tgc gcg ctc ttt gtg ctg            538
Asp Asp Val Leu Val His Leu Leu Ala Arg Cys Ala Leu Phe Val Leu
                150                 155                 160 gtg gct ccc agc tgc gcc tac cag gtg tgc ggg ccg ccg ctg tac cag            586
Val Ala Pro Ser Cys Ala Tyr Gln Val Cys Gly Pro Pro Leu Tyr Gln
            165                 170                 175 ctc ggc gct gcc act cag gcc cgg ccc ccg cca cac gct agt gga ccc            634
Leu Gly Ala Ala Thr Gln Ala Arg Pro Pro Pro His Ala Ser Gly Pro
            180                 185                 190 cga agg cgt ctg gga tgc gaa cgg gcc tgg aac cat agc gtc agg gag            682
Arg Arg Arg Leu Gly Cys Glu Arg Ala Trp Asn His Ser Val Arg Glu
            195                 200                 205 gcc ggg gtc ccc ctg ggc ctg cca gcc ccg ggt gcg agg agg cgc ggg            730
Ala Gly Val Pro Leu Gly Leu Pro Ala Pro Gly Ala Arg Arg Arg Gly
210                 215                 220                 225 ggc agt gcc agc cga agt ctg ccg ttg ccc aag agg ccc agg cgt ggc            778
Gly Ser Ala Ser Arg Ser Leu Pro Leu Pro Lys Arg Pro Arg Arg Gly
                230                 235                 240 gct gcc cct gag ccg gag cgg acg ccc gtt ggg cag ggg tcc tgg gcc            826
Ala Ala Pro Glu Pro Glu Arg Thr Pro Val Gly Gln Gly Ser Trp Ala
            245                 250                 255 cac ccg ggc agg acg cgt gga ccg agt gac cgt ggt ttc tgt gtg gtg            874
His Pro Gly Arg Thr Arg Gly Pro Ser Asp Arg Gly Phe Cys Val Val
            260                 265                 270 tca cct gcc aga ccc gcc gaa gaa gcc acc tct ttg gag ggt gcg ctc            922
Ser Pro Ala Arg Pro Ala Glu Glu Ala Thr Ser Leu Glu Gly Ala Leu
            275                 280                 285 tct ggc acg cgc cac tcc cac cca tcc gtg ggc gcc cag cac cac gcg            970
Ser Gly Thr Arg His Ser His Pro Ser Val Gly Arg Gln His His Ala
290                 295                 300                 305 ggc ccc cca tcc aca tcg cgg cca cca cgt ccc tgg gac acg cct tgt           1018
Gly Pro Pro Ser Thr Ser Arg Pro Pro Arg Pro Trp Asp Thr Pro Cys
                310                 315                 320 ccc ccg gtg tac gcc gag acc aag cac ttc ctc tac tcc tca ggc gac           1066
Pro Pro Val Tyr Ala Glu Thr Lys His Phe Leu Tyr Ser Ser Gly Asp
            325                 330                 335 aag gag cag ctg cgg ccc tcc ttc cta ctc agc tct ctg agg ccc agc           1114
Lys Glu Gln Leu Arg Pro Ser Phe Leu Leu Ser Ser Leu Arg Pro Ser
            340                 345                 350 ctg act ggc gct cgg agg ctc gtg gag acc atc ttt ctg ggt tcc agg           1162
Leu Thr Gly Ala Arg Arg Leu Val Glu Thr Ile Phe Leu Gly Ser Arg
355                 360                 365 ccc tgg atg cca ggg act ccc cgc agg ttg ccc cgc ctg ccc cag cgc           1210
Pro Trp Met Pro Gly Thr Pro Arg Arg Leu Pro Arg Leu Pro Gln Arg
370                 375                 380                 385
```

```
tac tgg caa atg cgg ccc ctg ttt ctg gag ctg ctt ggg aac cac gcg      1258
Tyr Trp Gln Met Arg Pro Leu Phe Leu Glu Leu Leu Gly Asn His Ala
                390                 395                 400 cag tgc ccc tac ggg gtg ctc ctc aag acg cac tgc ccg ctg cga gct      1306
Gln Cys Pro Tyr Gly Val Leu Leu Lys Thr His Cys Pro Leu Arg Ala
            405                 410                 415 gcg gtc acc cca gca gcc ggt gtc tgt gcc cgg gag aag ccc cag ggc      1354
Ala Val Thr Pro Ala Ala Gly Val Cys Ala Arg Glu Lys Pro Gln Gly
        420                 425                 430 tct gtg gcg gcc ccc gag gag gag gac aca gac ccc cgt cgc ctg gtg      1402
Ser Val Ala Ala Pro Glu Glu Glu Asp Thr Asp Pro Arg Arg Leu Val
    435                 440                 445 cag ctg ctc cgc cag cac agc agc ccc tgg cag gtg tac ggc ttc gtg      1450
Gln Leu Leu Arg Gln His Ser Ser Pro Trp Gln Val Tyr Gly Phe Val
450                 455                 460                 465 cgg gcc tgc ctg cgc cgg ctg gtg ccc cca ggc ctc tgg ggc tcc agg      1498
Arg Ala Cys Leu Arg Arg Leu Val Pro Pro Gly Leu Trp Gly Ser Arg
                470                 475                 480 cac aac gaa cgc cgc ttc ctc agg aac acc aag aag ttc atc tcc ctg      1546
His Asn Glu Arg Arg Phe Leu Arg Asn Thr Lys Lys Phe Ile Ser Leu
            485                 490                 495 ggg aag cat gcc aag ctc tcg ctg cag gag ctg acg tgg aag atg agc      1594
Gly Lys His Ala Lys Leu Ser Leu Gln Glu Leu Thr Trp Lys Met Ser
        500                 505                 510 gtg cgg gac tgc gct tgg ctg cgc agg agc cca ggg gtt ggc tgt gtt      1642
Val Arg Asp Cys Ala Trp Leu Arg Arg Ser Pro Gly Val Gly Cys Val
    515                 520                 525 ccg gcc gca gag cac cgt ctg cgt gag gag atc ctg gcc aag ttc ctg      1690
Pro Ala Ala Glu His Arg Leu Arg Glu Glu Ile Leu Ala Lys Phe Leu
530                 535                 540                 545 cac tgg ctg atg agt gtg tac gtc gtc gag ctg ctc agg tct ttc ttt      1738
His Trp Leu Met Ser Val Tyr Val Val Glu Leu Leu Arg Ser Phe Phe
                550                 555                 560 tat gtc acg gag acc acg ttt caa aag aac agg ctc ttt ttc tac cgg      1786
Tyr Val Thr Glu Thr Thr Phe Gln Lys Asn Arg Leu Phe Phe Tyr Arg
            565                 570                 575 aag agt gtc tgg agc aag ttg caa agc att gga atc aga cag cac ttg      1834
Lys Ser Val Trp Ser Lys Leu Gln Ser Ile Gly Ile Arg Gln His Leu
        580                 585                 590 aag agg gtg cag ctg cgg gag ctg tcg gaa gca gag gtc agg cag cat      1882
Lys Arg Val Gln Leu Arg Glu Leu Ser Glu Ala Glu Val Arg Gln His
    595                 600                 605 cgg gaa gcc agg ccc gcc ctg ctg acg tcc aga ctc cgc ttc atc ccc      1930
Arg Glu Ala Arg Pro Ala Leu Leu Thr Ser Arg Leu Arg Phe Ile Pro
610                 615                 620                 625 aag cct gac ggg ctg cgg ccg att gtg aac atg gac tac gtc gtg gga      1978
Lys Pro Asp Gly Leu Arg Pro Ile Val Asn Met Asp Tyr Val Val Gly
                630                 635                 640 gcc aga acg ttc cgc aga gaa aag agg gcc gag cgt ctc acc tcg agg      2026
Ala Arg Thr Phe Arg Arg Glu Lys Arg Ala Glu Arg Leu Thr Ser Arg
            645                 650                 655 gtg aag gca ctg ttc agc gtg ctc aac tac gag cgg gcg cgg cgc ccc      2074
Val Lys Ala Leu Phe Ser Val Leu Asn Tyr Glu Arg Ala Arg Arg Pro
        660                 665                 670 ggc ctc ctg ggc gcc tct gtg ctg ggc ctg gac gat atc cac agg gcc      2122
Gly Leu Leu Gly Ala Ser Val Leu Gly Leu Asp Asp Ile His Arg Ala
    675                 680                 685 tgg cgc acc ttc gtg ctg cgt gtg cgg gcc cag gac ccg ccg cct gag      2170
Trp Arg Thr Phe Val Leu Arg Val Arg Ala Gln Asp Pro Pro Pro Glu
690                 695                 700                 705
```

-continued

```
ctg tac ttt gtc aag gtg gat gtg acg ggc gcg tac gac acc atc ccc      2218
Leu Tyr Phe Val Lys Val Asp Val Thr Gly Ala Tyr Asp Thr Ile Pro
            710                 715                 720 cag gac agg ctc acg gag gtc atc gcc agc atc atc aaa ccc cag aac      2266
Gln Asp Arg Leu Thr Glu Val Ile Ala Ser Ile Ile Lys Pro Gln Asn
        725                 730                 735 acg tac tgc gtg cgt cgg tat gcc gtg gtc cag aag gcc gcc cat ggg      2314
Thr Tyr Cys Val Arg Arg Tyr Ala Val Val Gln Lys Ala Ala His Gly
    740                 745                 750 cac gtc cgc aag gcc ttc aag agc cac gtc tct acc ttg aca gac ctc      2362
His Val Arg Lys Ala Phe Lys Ser His Val Ser Thr Leu Thr Asp Leu
755                 760                 765 cag ccg tac atg cga cag ttc gtg gct cac ctg cag gag acc agc ccg      2410
Gln Pro Tyr Met Arg Gln Phe Val Ala His Leu Gln Glu Thr Ser Pro
770                 775                 780                 785 ctg agg gat gcc gtc gtc atc gag cag agc tcc tcc ctg aat gag gcc      2458
Leu Arg Asp Ala Val Val Ile Glu Gln Ser Ser Ser Leu Asn Glu Ala
                790                 795                 800 agc agt ggc ctc ttc gac gtc ttc cta cgc ttc atg tgc cac cac gcc      2506
Ser Ser Gly Leu Phe Asp Val Phe Leu Arg Phe Met Cys His His Ala
            805                 810                 815 gtg cgc atc agg ggc aag tcc tac gtc cag tgc cag ggg atc ccg cag      2554
Val Arg Ile Arg Gly Lys Ser Tyr Val Gln Cys Gln Gly Ile Pro Gln
        820                 825                 830 ggc tcc atc ctc tcc acg ctg ctc tgc agc ctg tgc tac ggc gac atg      2602
Gly Ser Ile Leu Ser Thr Leu Leu Cys Ser Leu Cys Tyr Gly Asp Met
    835                 840                 845 gag aac aag ctg ttt gcg ggg att cgg cgg gac ggg ctg ctc ctg cgt      2650
Glu Asn Lys Leu Phe Ala Gly Ile Arg Arg Asp Gly Leu Leu Leu Arg
850                 855                 860                 865 ttg gtg gat gat ttc ttg ttg gtg aca cct cac ctc acc cac gcg aaa      2698
Leu Val Asp Asp Phe Leu Leu Val Thr Pro His Leu Thr His Ala Lys
                870                 875                 880 acc ttc ctc agg acc ctg gtc cga ggt gtc cct gag tat ggc tgc gtg      2746
Thr Phe Leu Arg Thr Leu Val Arg Gly Val Pro Glu Tyr Gly Cys Val
            885                 890                 895 gtg aac ttg cgg aag aca gtg gtg aac ttc cct gta gaa gac gag gcc      2794
Val Asn Leu Arg Lys Thr Val Val Asn Phe Pro Val Glu Asp Glu Ala
        900                 905                 910 ctg ggt ggc acg gct ttt gtt cag atg ccg gcc cac ggc cta ttc ccc      2842
Leu Gly Gly Thr Ala Phe Val Gln Met Pro Ala His Gly Leu Phe Pro
    915                 920                 925 tgg tgc ggc ctg ctg ctg gat acc cgg acc ctg gag gtg cag agc gac      2890
Trp Cys Gly Leu Leu Leu Asp Thr Arg Thr Leu Glu Val Gln Ser Asp
930                 935                 940                 945 tac tcc agc tat gcc cgg acc tcc atc aga gcc agt ctc acc ttc aac      2938
Tyr Ser Ser Tyr Ala Arg Thr Ser Ile Arg Ala Ser Leu Thr Phe Asn
                950                 955                 960 cgc ggc ttc aag gct ggg agg aac atg cgt cgc aaa ctc ttt ggg gtc      2986
Arg Gly Phe Lys Ala Gly Arg Asn Met Arg Arg Lys Leu Phe Gly Val
            965                 970                 975 ttg cgg ctg aag tgt cac agc ctg ttt ctg gat ttg cag gtg aac agc      3034
Leu Arg Leu Lys Cys His Ser Leu Phe Leu Asp Leu Gln Val Asn Ser
        980                 985                 990 ctc cag acg gtg tgc acc aac atc tac aag atc ctc ctg ctg cag gcg      3082
Leu Gln Thr Val Cys Thr Asn Ile Tyr Lys Ile Leu Leu Leu Gln Ala
    995                 1000                1005 tac agg ttt cac gca tgt gtg ctg cag ctc cca ttt cat cag caa         3127
Tyr Arg Phe His Ala Cys Val Leu Gln Leu Pro Phe His Gln Gln
```

-continued

| | | |
|---|---|---|
| gtt tgg aag aac ccc aca ttt ttc ctg cgc gtc atc tct gac acg<br>Val Trp Lys Asn Pro Thr Phe Phe Leu Arg Val Ile Ser Asp Thr<br>1025               1030               1035 | | 3172 |
| gcc tcc ctc tgc tac tcc atc ctg aaa gcc aag aac gca ggg atg<br>Ala Ser Leu Cys Tyr Ser Ile Leu Lys Ala Lys Asn Ala Gly Met<br>1040               1045               1050 | | 3217 |
| tcg ctg ggg gcc aag ggc gcc gcc ggc cct ctg ccc tcc gag gcc<br>Ser Leu Gly Ala Lys Gly Ala Ala Gly Pro Leu Pro Ser Glu Ala<br>1055               1060               1065 | | 3262 |
| gtg cag tgg ctg tgc cac caa gca ttc ctg ctc aag ctg act cga<br>Val Gln Trp Leu Cys His Gln Ala Phe Leu Leu Lys Leu Thr Arg<br>1070               1075               1080 | | 3307 |
| cac cgt gtc acc tac gtg cca ctc ctg ggg tca ctc agg aca gcc<br>His Arg Val Thr Tyr Val Pro Leu Leu Gly Ser Leu Arg Thr Ala<br>1085               1090               1095 | | 3352 |
| cag acg cag ctg agt cgg aag ctc ccg ggg acg acg ctg act gcc<br>Gln Thr Gln Leu Ser Arg Lys Leu Pro Gly Thr Thr Leu Thr Ala<br>1100               1105               1110 | | 3397 |
| ctg gag gcc gca gcc aac ccg gca ctg ccc tca gac ttc aag acc<br>Leu Glu Ala Ala Ala Asn Pro Ala Leu Pro Ser Asp Phe Lys Thr<br>1115               1120               1125 | | 3442 |
| atc ctg gac tga tggccacccg cccacagcca ggccgagagc agacaccagc<br>Ile Leu Asp<br>1130 | | 3494 |
| agccctgtca cgccgggctc tacgtcccag ggagggaggg gcggcccaca cccaggcccg | | 3554 |
| caccgctggg agtctgaggc ctgagtgagt gtttggccga ggcctgcatg tccggctgaa | | 3614 |
| ggctgagtgt ccggctgagg cctgagcgag tgtccagcca agggctgagt gtccagcaca | | 3674 |
| cctgccgtct tcacttcccc acaggctggc gctcggctcc accccagggc cagcttttcc | | 3734 |
| tcaccaggag cccggcttcc actccccaca taggaatagt ccatcccag attcgccatt | | 3794 |
| gttcacccct cgccctgccc tcctttgcct tccacccca catccaggt ggagaccctg | | 3854 |
| agaaggaccc tgggagctct gggaatttgg agtgaccaaa ggtgtgccct gtacacaggc | | 3914 |
| gaggaccctg cacctggatg ggggtccctg tgggtcaaat tggggggagg tgctgtggga | | 3974 |
| gtaaaatact gaatatatga gtttttcagt tttgaaaaaa a | | 4015 |

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1              5                 10                15

His Tyr Arg Glu Val Leu Pro Leu Ala Thr Phe Val Arg Arg Leu Gly
           20                 25                30

Pro Gln Gly Trp Arg Leu Val Gln Arg Gly Asp Pro Ala Ala Phe Arg
        35                40               45

Ala Leu Val Ala Gln Cys Leu Val Cys Val Pro Trp Asp Ala Arg Pro
    50                55               60

Pro Pro Ala Ala Pro Ser Phe Arg Gln Val Ser Cys Leu Lys Glu Leu
65              70               75               80

Val Ala Arg Val Leu Gln Arg Leu Cys Glu Arg Gly Ala Lys Asn Val
           85                 90                95

Leu Ala Phe Gly Phe Ala Leu Leu Asp Gly Ala Arg Gly Gly Pro Pro

-continued

```
                100             105             110
Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Arg Arg Val
        130                 135                 140

Gly Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro His Ala Ser Gly
        180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
        210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
    290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
        355                 360                 365

Arg Pro Trp Met Pro Gly Thr Pro Arg Arg Leu Pro Arg Leu Pro Gln
    370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Asp Thr Asp Pro Arg Arg Leu
        435                 440                 445

Val Gln Leu Leu Arg Gln His Ser Ser Pro Trp Gln Val Tyr Gly Phe
    450                 455                 460

Val Arg Ala Cys Leu Arg Arg Leu Val Pro Pro Gly Leu Trp Gly Ser
465                 470                 475                 480

Arg His Asn Glu Arg Arg Phe Leu Arg Asn Thr Lys Lys Phe Ile Ser
                485                 490                 495

Leu Gly Lys His Ala Lys Leu Ser Leu Gln Glu Leu Thr Trp Lys Met
            500                 505                 510

Ser Val Arg Asp Cys Ala Trp Leu Arg Arg Ser Pro Gly Val Gly Cys
        515                 520                 525
```

```
Val Pro Ala Ala Glu His Arg Leu Arg Glu Ile Leu Ala Lys Phe
    530                 535                 540

Leu His Trp Leu Met Ser Val Tyr Val Glu Leu Leu Arg Ser Phe
545                 550                 555                 560

Phe Tyr Val Thr Glu Thr Thr Phe Gln Lys Asn Arg Leu Phe Phe Tyr
                565                 570                 575

Arg Lys Ser Val Trp Ser Lys Leu Gln Ser Ile Gly Ile Arg Gln His
            580                 585                 590

Leu Lys Arg Val Gln Leu Arg Glu Leu Ser Glu Ala Glu Val Arg Gln
        595                 600                 605

His Arg Glu Ala Arg Pro Ala Leu Leu Thr Ser Arg Leu Arg Phe Ile
    610                 615                 620

Pro Lys Pro Asp Gly Leu Arg Pro Ile Val Asn Met Asp Tyr Val Val
625                 630                 635                 640

Gly Ala Arg Thr Phe Arg Arg Glu Lys Arg Ala Glu Arg Leu Thr Ser
                645                 650                 655

Arg Val Lys Ala Leu Phe Ser Val Leu Asn Tyr Glu Arg Ala Arg Arg
            660                 665                 670

Pro Gly Leu Leu Gly Ala Ser Val Leu Gly Leu Asp Asp Ile His Arg
        675                 680                 685

Ala Trp Arg Thr Phe Val Leu Arg Val Arg Ala Gln Asp Pro Pro
    690                 695                 700

Glu Leu Tyr Phe Val Lys Val Asp Val Thr Gly Ala Tyr Asp Thr Ile
705                 710                 715                 720

Pro Gln Asp Arg Leu Thr Glu Val Ile Ala Ser Ile Ile Lys Pro Gln
                725                 730                 735

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
        755                 760                 765

Leu Gln Pro Tyr Met Arg Gln Phe Val Ala His Leu Gln Glu Thr Ser
770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
            820                 825                 830

Gln Gly Ser Ile Leu Ser Thr Leu Leu Cys Ser Leu Cys Tyr Gly Asp
        835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
            900                 905                 910

Ala Leu Gly Gly Thr Ala Phe Val Gln Met Pro Ala His Gly Leu Phe
        915                 920                 925

Pro Trp Cys Gly Leu Leu Leu Asp Thr Arg Thr Leu Glu Val Gln Ser
930                 935                 940
```

-continued

```
Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
        995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130
```

TREATMENT FOR WOUNDS

CROSS-REFERENCE TO RELATED APPLICATIONS

This application claims the priority benefit of U.S. provisional patent application No. 60/289,903, filed May 9, 2001, pending. The priority application is hereby incorporated herein by reference in its entirety.

TECHNICAL FIELD

This invention relates to the field of the cell biology of epidermal cells and the substratum, and enhancement of the properties of these tissues for purposes of therapy. The invention also relates to the enzyme telomerase reverse transcriptase, and its use in regulating telomerase length.

BACKGROUND

The worldwide chronic skin wound market, which includes diabetic foot ulcers, venous stasis ulcers and bedsores, is estimated to bear over $6 billion annually in treatment costs. The number of patients is about 12.5 million. The largest proportion is the venous stasis market, estimated at $3 billion annually, or 3.6 million patients. Venous leg ulcers are a type of chronic wound that affects up to 1 million people in the U.S., 90% of whom are over age 50. Skin lesions also present for medical treatment following accidents that involve abrasion or burning of the dermis.

Pharmaceuticals under development for managing these conditions include compositions that promote activity of endogenous cells at the site of the wound.

The family of keratinocyte growth factors has been implicated in the process of wound healing. Beer et al. (J. Investig. Dermatol. Symp. Proc. 5:34, 2000) showed that KGF is weakly expressed in healthy human skin, but strongly upregulated in dermal fibroblasts after skin injury. Binding to a transmembrane receptor on keratinocytes induces both proliferation and migration of the cells, and protects them from toxic effects of reactive oxygen species. Soler et al. (Wound Repair Regen. 7:172, 1999) characterized KGF-2 as a potential wound healing agent. It was found to increase both proliferation and migration of keratinocytes, and promote healing of human meshed skin explanted grafts and surgical excisions.

U.S. Pat. Nos. 5,814,605 and 5,965,530 provide pharmaceutical compositions comprising keratinocyte growth factor (KGF-1), for use in reducing hair loss. U.S. Pat. No. 6,077,602 relates to the sequence of keratinocyte growth factor 2 (KGF-2) and variants with enhanced activity and stability, for use in promoting wound healing. KGF-2 is currently being evaluated in clinical trials for treating injuries and skin disorders.

Other options that have been proposed for promoting activity in cells near the wound include the following. U.S. Pat. No. 5,718,897 outlines a method of enhancing migration and proliferation of keratinocytes in wound healing, by treating the wound with collagenase and a growth factor. U.S. Pat. No. 5,997,863 outlines a method of enhancing wound healing by administering enzymes that degrade glycosaminoglycans such as heparin or chondroitin sulfate in various combinations. Inada et al. (Am. J. Pathol. 157:1875, 2000) propose to facilitate wound healing by activating the transglutaminase-1 gene. Jaakkola et al. (Gene Ther. 7:1640, 2000) used adenovirus to deliver the gene for growth factor inducible element named "FIRE" into wound margin keratinocytes. U.S. Pat. No. 6,001,805 provides a method of enhancing wound healing by stimulating fibroblast and keratinocyte growth in vivo using amphipathic peptides. U.S. Pat. No. 6,191,110 outlines a method of enhancing wound healing by stimulating fibroblast and keratinocyte in vivo using amphipathic peptides of a particular sequence.

Other compositions for promoting wound healing including isolated cells and cell matrices derived from the subject being treated or a third-party donor, and adapted to provide protection of the wound while healing takes place.

U.S. Pat. No. 5,980,888 relates to a biomaterial designed for treating skin wounds, in which keratinocytes are attached to microcarrier beads of 50-500 microns in diameter. International Patent Publication WO 97/08295 outlines a reconstituted skin, comprising a dermal matrix inoculated with epithelial cells or their progenitors. U.S. Pat. No. 5,861,153 outlines a skin equivalent, comprising a support, isolated keratinocytes, and Langerhans' cells that have been activated by culturing with keratinocytes or growth factors. U.S. Pat. No. 5,580,781 reports a method for treating a skin defect by applying epidermal tissue comprising cultured outer root sheath cells. U.S. Pat. No. 6,110,208 outlines an artificial human skin comprising a support comprising a microperforated membrane upon which keratinocytes have been seeded, and an underlying tissue upon which fibroblasts have been seeded.

Genetically modified epithelial cells have been investigated in several contexts. U.S. Pat. Nos. 4,868,116, 4,980,286, and 5,698,436 relate to the introduction and expression of foreign genetic material in epithelial cells. International Patent Publication WO 97/23602 outlines techniques for obtaining human skin cell lines that have been immortalized with the SF40 large T antigen, or the E6/E7 gene of HPV16.

In 1998, Organogenesis received FDA marketing clearance for its full-thickness artificial skin product, Apligraf®, for treating venous stasis wounds. Like human skin, the product has two primary layers, an outer epidermal layer made of living human keratinocytes, the most common cell type of the human epidermis, and an inner dermal layer consisting of living human fibroblasts, the most common cell type in the human dermis. The human keratinocytes and fibroblasts used in its manufacture are derived from donor tissue. Apligraf® is currently approved for treating venous leg ulcers and diabetic foot ulcers.

The considerable complexity of the wound healing process is reviewed in Science magazine (P. Martin, Science 276:75, 1997). The article takes the view that normal adult wound repair is less like patching and more like regeneration. In view of the pervasive presence of skin lesions in our aging population, there is a compelling need for new modalities in wound healing.

SUMMARY

This disclosure provides materials and methods for treating wounds. Some aspects of the invention relate to agents that activate degenerative epithelial cells to restore normal mobility, resist apoptosis, and increase their proliferative capacity. The agents increase telomerase activity in epithelial cells and other cells present near a wound site, promoting the cells to move to the site and restore an epithelial layer. Other aspects of the invention relate to compositions comprising epithelial cells in which telomerase activity has been increased, useful as grafts in the treatment of wounds.

One embodiment of the invention is a pharmaceutical composition comprising a vector encoding telomerase reverse transcriptase (TERT), or other agent that increases telomerase activity or expression, formulated for administration to a wound site or an epithelial surface, such as the skin. The agent may be provided in a suitable excipient, such as a cream or gel, which may contain a constituent that enhances penetration or resistance to proteases, or otherwise enhances or prolongs efficiency. The composition may cause transient TERT expression in cells at the wound site if it is an adenovirus or lipid vector, or permanent TERT expression in cells and their progeny if it is a retrovirus vector. Some of the many effects possible are that epithelial cells treated with the composition express certain levels of telomerase activity (as measured in a TRAP assay), the ability to migrate on a solid surface at a substantial rate, or secretion of factors or matrix materials that promote wound closing.

Another embodiment of the invention is a pharmaceutical composition comprising telomerized epithelial cells or fibroblasts. The composition may further comprise a microparticle or matrix to enhance administration to a wound site or an epithelial surface, such as the skin, and may be further accompanied by a matrix or dressing for attaching the cells to a treatment site. In certain circumstances, the telomerized cells in the composition may express certain levels of telomerase activity, or the ability to migrate on a solid surface at a substantial rate.

Other embodiments of the invention relate to treating a wound or an epithelial cell surface, using a pharmaceutical composition of this invention. Exemplary are compositions containing a vector encoding telomerase reverse transcriptase (TERT), or compositions containing telomerized epithelial cells. Included are methods in which an agent is applied that causes increased expression of TERT in cells at the wound site. Subsequently, the treatment site can be monitored for effect of the composition, such as closing of the wound or reepithelialization of the surface. Administering the composition may have a number of beneficial effects, such as enhancing wound closure compared with an untreated wound, increasing TERT activity or expression in any restorative cell type present in the wound.

Another embodiment of the invention is a method of increasing migration of an epithelial cell, comprising causing increased telomerase activity in the epithelial cell (for example, by causing increased expression of TERT in the cell). The cell may subsequently be monitored for the effect of treatment, such as telomerase activity, or the ability to migrate on a solid surface.

Another embodiment of the invention is a method for screening a compound for its ability to affect cell migration, epithelialization, or wound healing, either in vitro or in vivo. For example, the compound can be contacted with telomerized epithelial cells in culture, and the effect on migration can be determined. Alternatively, the compound can be administered to an epithelial surface comprising telomerized cells on a living subject, and the effect on the treated cells can be determined.

The pharmaceutical methods and treatment compositions can be used for any therapeutically desirable purpose, including the treatment of any epithelial surface for wounds or any other perceived imperfection. The invention is particularly suitable for treating acute lesions, such as a traumatic lesion, burn, or surgical incision; and chronic lesions, such as a chronic venous ulcer, diabetic ulcer, or compression ulcer.

Other aspects of the invention will be apparent from the description that follows.

DRAWINGS

Figure 3:
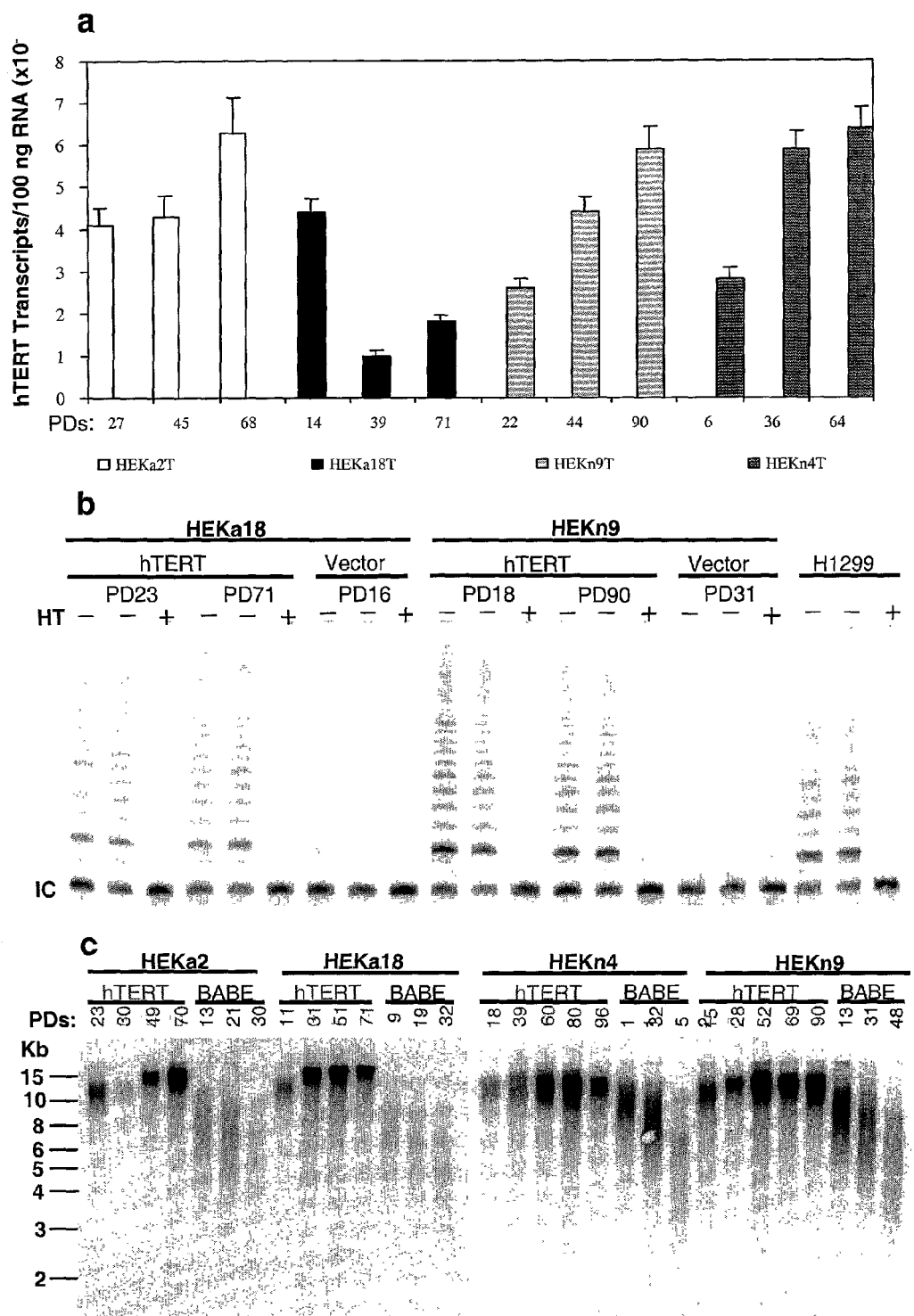

FIG. 3 shows that transduction of keratinocytes with the TERT retrovirus causes TERT expression, increased telomerase activity, and lengthening of telomerase. Panel (a) shows quantitation of hTERT transcripts determined by RT-PCR. Panel (b) shows telomerase activity in cell lysate, as detected by TRAP assay. The H1299 tumor cell line is a positive control. Panel (c) shows telomere terminal restriction fragment lengths of human TERT transduced keratinocytes, and vector control (BABE).

Figure 4:
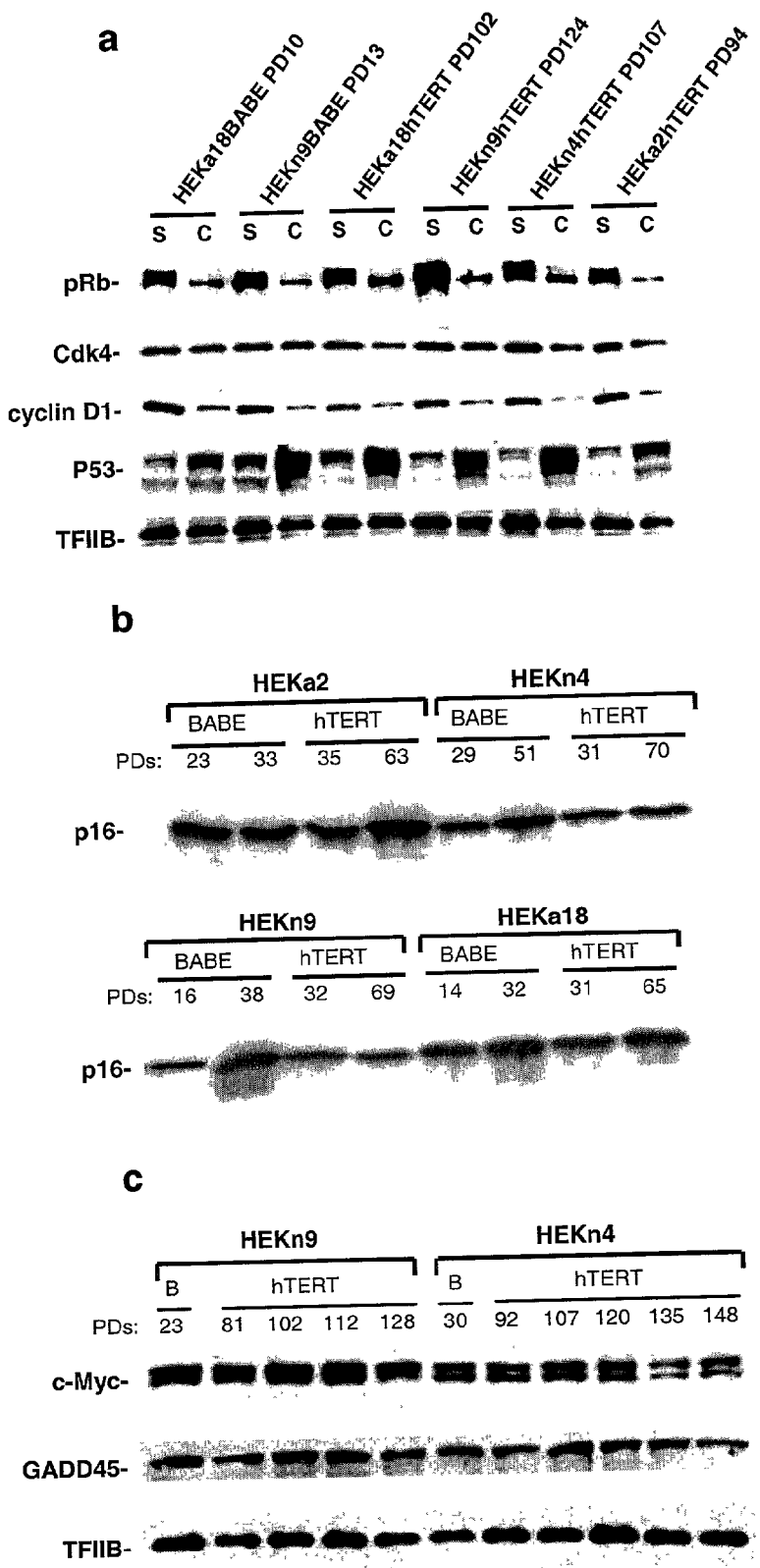

FIG. 4 shows that transduced keratinocytes have normal expression of cell cycle regulation proteins and c-myc.

Figure 5:
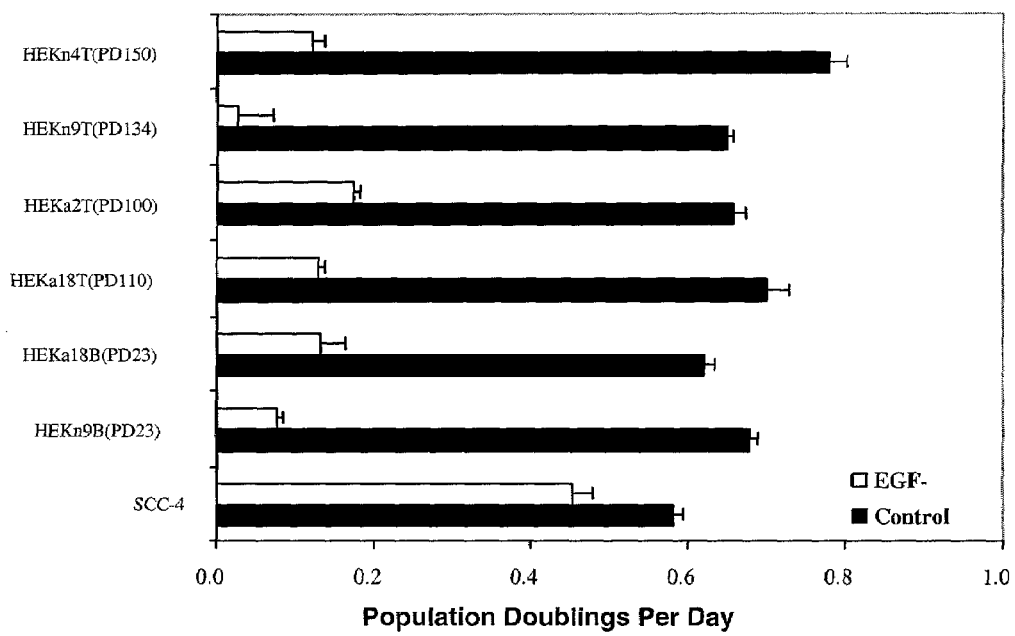
Figure 5:
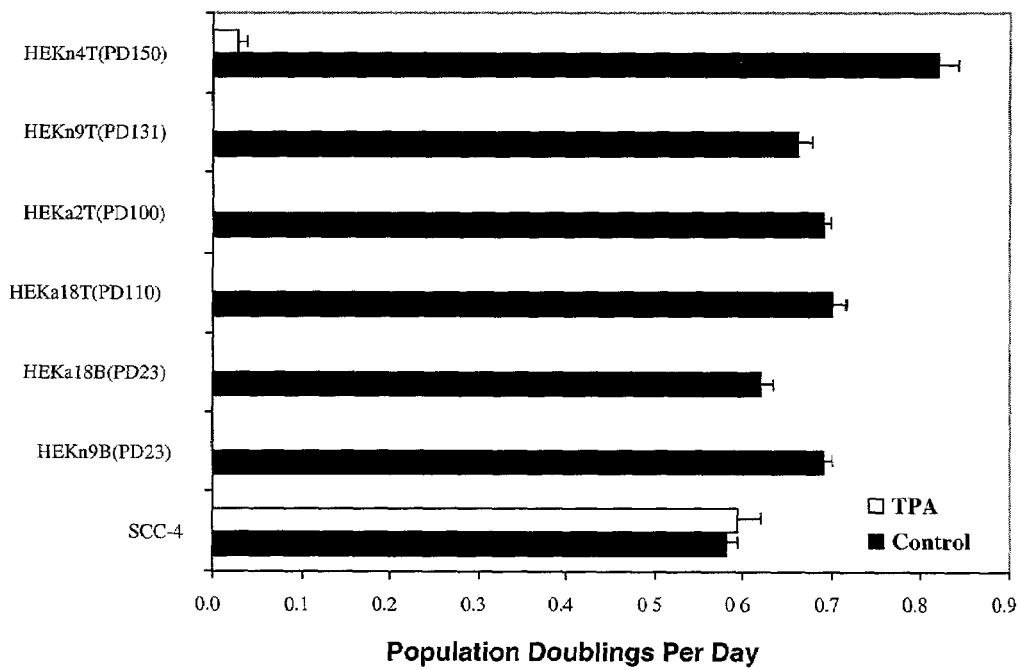

FIG. 5 shows that growth of transduced keratinocytes is dependent on epidermal growth factor (EGF), and sensitive to phorbol ester (TPA), characteristic of normal growth control (i.e., a non-malignant phenotype).

Figure 6:
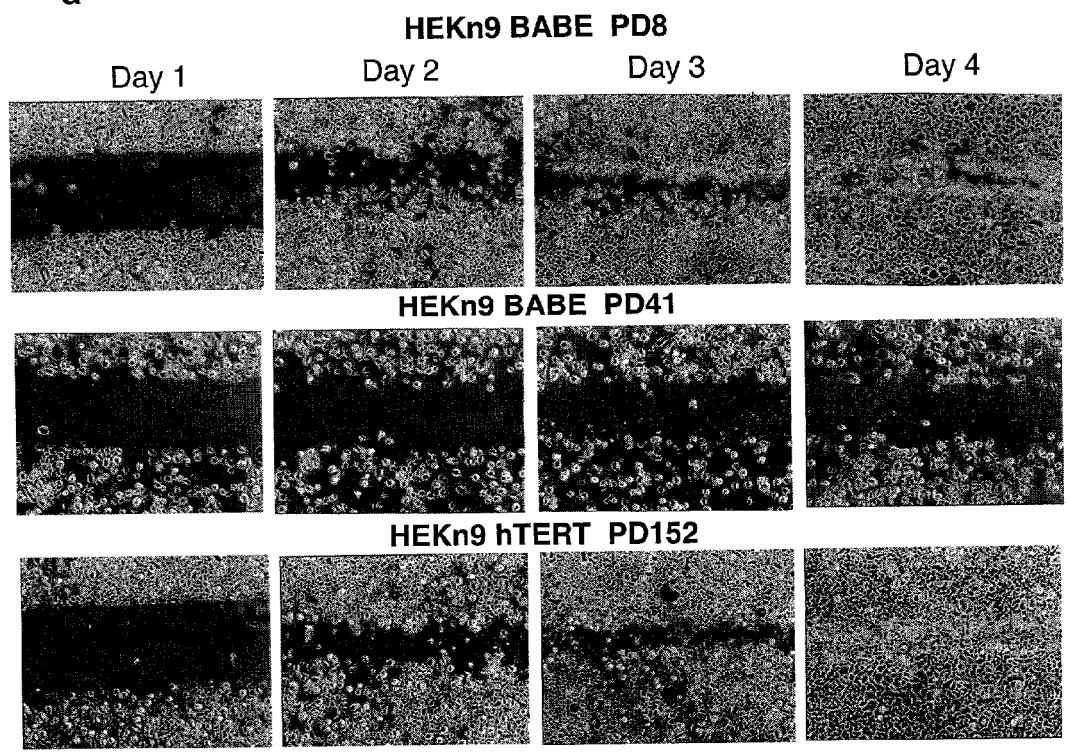
Figure 6:
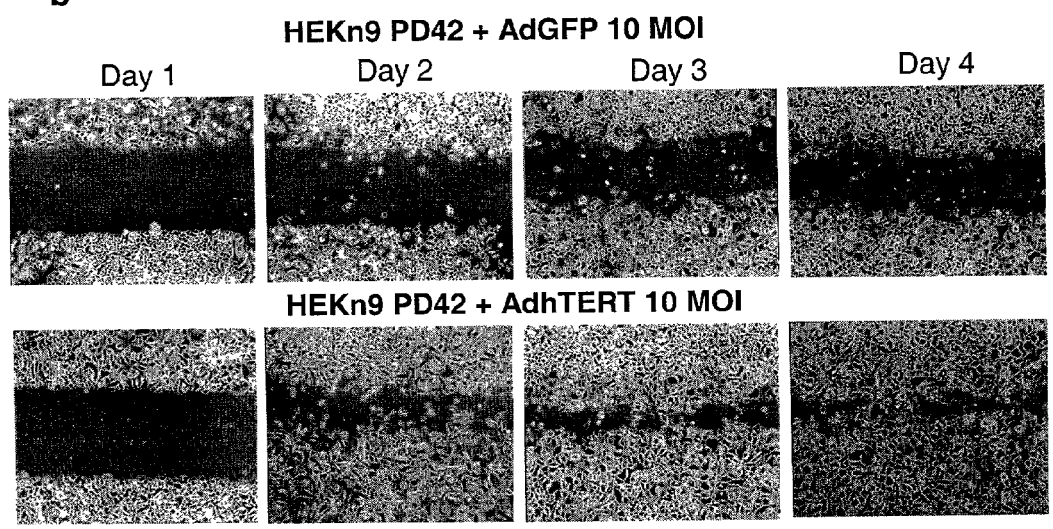

FIG. 6 shows the behaviour of keratinocytes in a wound healing model. Keratinocytes were grown to near confluence, and then a 1 mm streak was cleared to determine keratinocyte migration over the next 4 days.

Panel (a) shows results of the HEKn9 neonatal keratinocyte line transduced early in culture with the human TERT retrovirus vector, or with vector control (BABE). TERT expressing keratinocytes taken to 152 population doublings retained migration characteristics of very young cells (PD8), which is at least 3-fold higher than the migration rate usually observed in keratinocytes reaching their doubling limit (PD41).

Panel (b) shows results of old HEKn9 cells (PD41) transduced with adenovirus vector for transient expression of hTERT, or with vector control (AdGFP). Short-term induction of telomerase activity in these cells restored their ability to close the wound.

Figure 7:
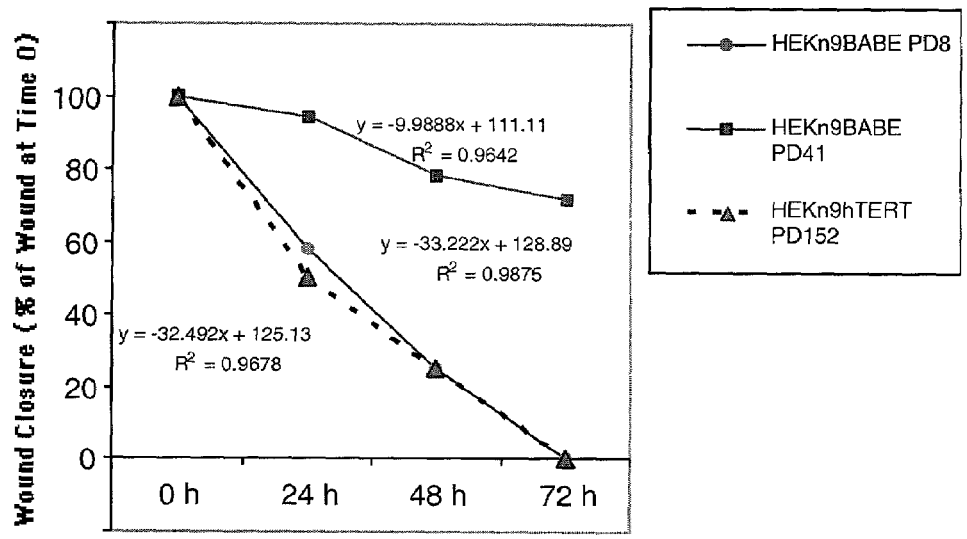
Figure 7:
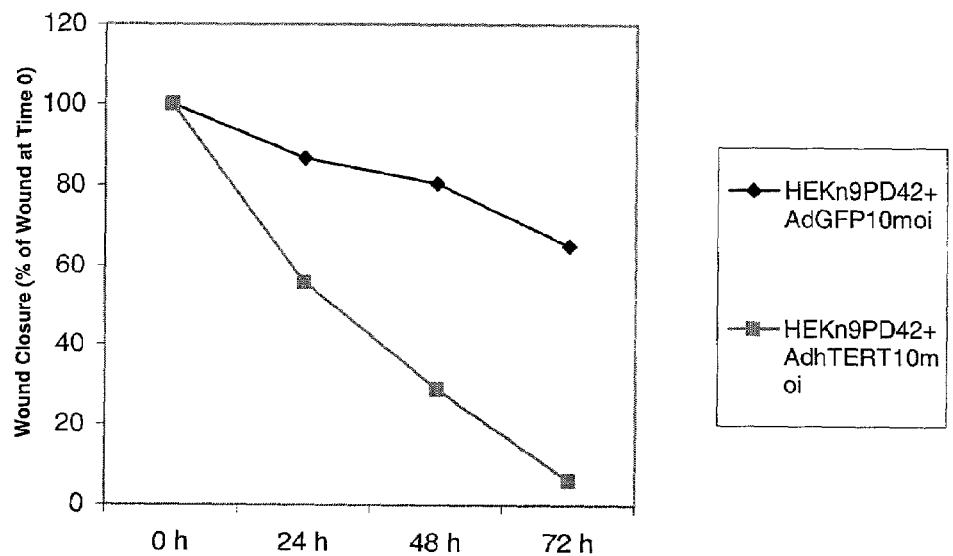

FIG. 7 shows the rate of wound closure following transduction of late-passage HEKn9 keratinocytes for increased expression of TERT (or vector control). Either long-term TERT expression (from retrovirus transduction) or transient expression from adenovirus transduction) caused a comparable acceleration in wound healing over the 4-day period.

Figure 8:
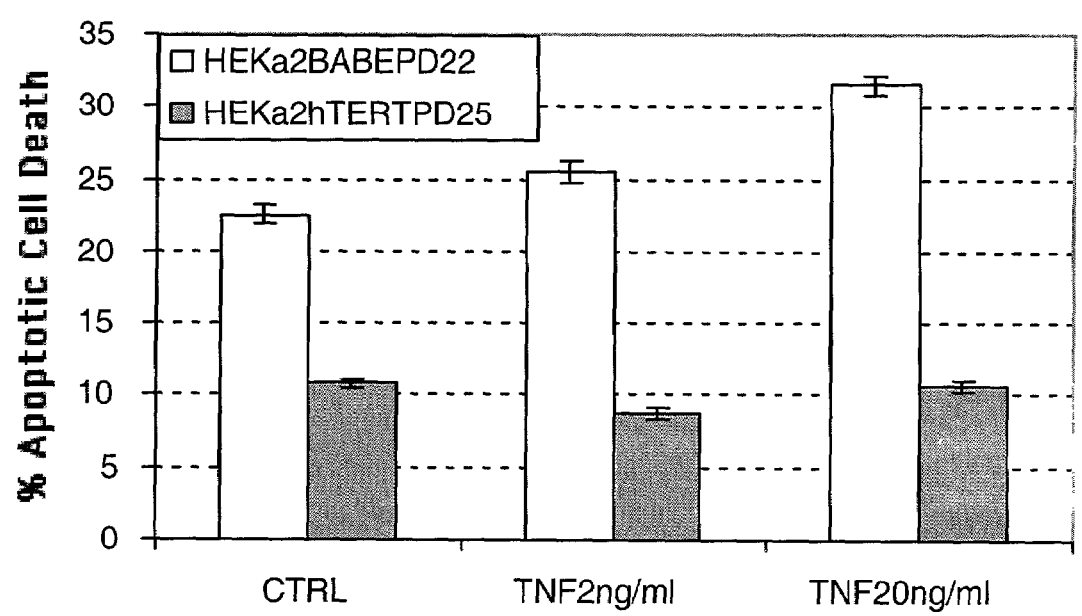

FIG. 8 is from an experiment in which TNF-α induced apoptosis of keratinocytes was measured by Annexin V staining. HEKa2 keratinocytes treated with vector control (open bars) were ~20% susceptible to apoptotic cell death, which increased in the presence of TNF-α. However, telomerized keratinocytes (stippled bars) showed lower levels of apoptosis, and were resistant to the effects of TNF-α.

Figure 9:
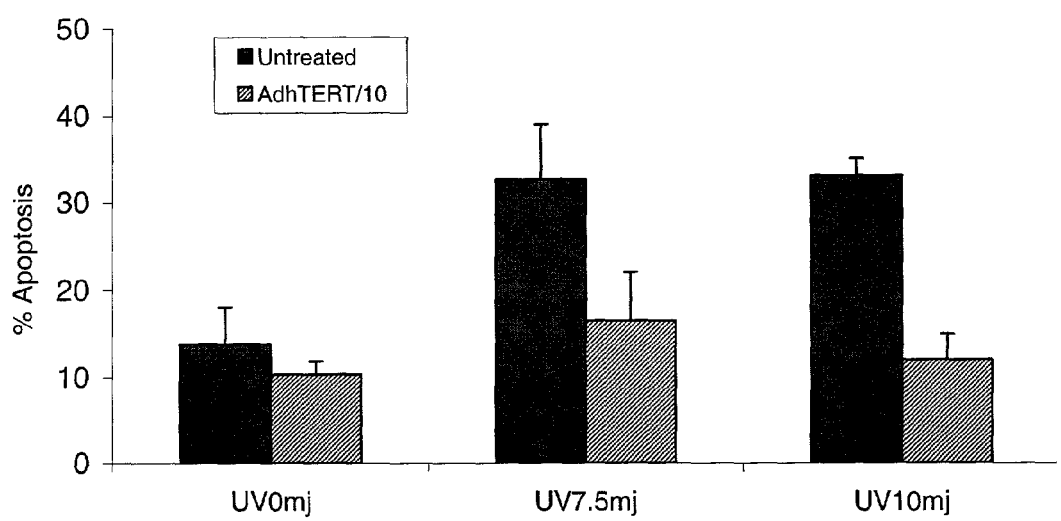
Figure 9:
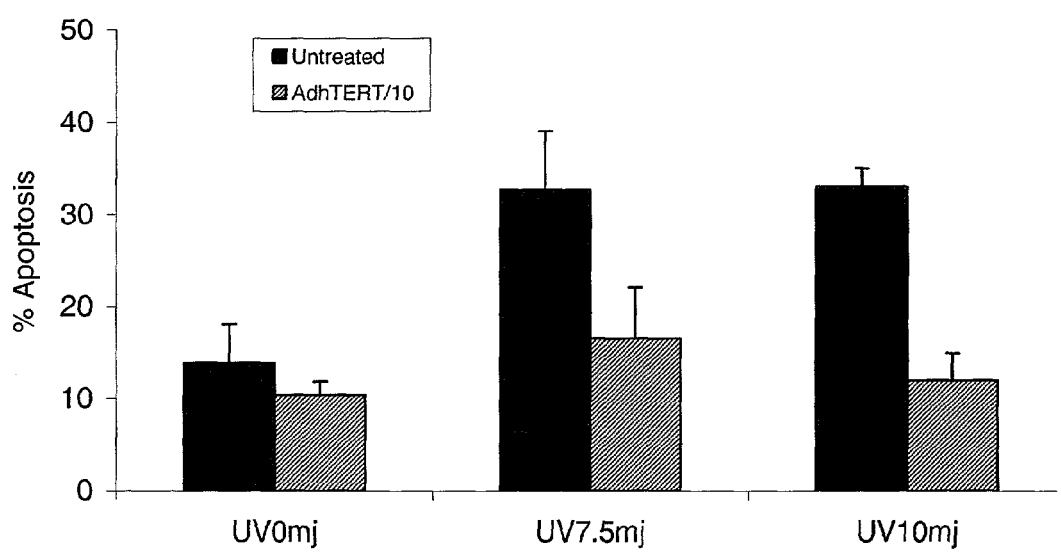

FIG. 9 shows that TERT also protects keratinocytes against UV irradiation induced apoptosis. For the top graph, cells were transfected with an adenovirus expressing hTERT for 3 days, irradiated for 24 h, then stained with Annexin V. hTERT stabilized the cells against apoptosis to control levels after UV irradiation up to 10 mJ cm$^{-1}$. For the bottom graph, the cells were allowed to proliferate for 5 days between hTERT transfection and UV irradiation. The protective effect of hTERT is still present, suggesting that resistance to apoptosis may ensue from increased telomere length.

Figure 10:
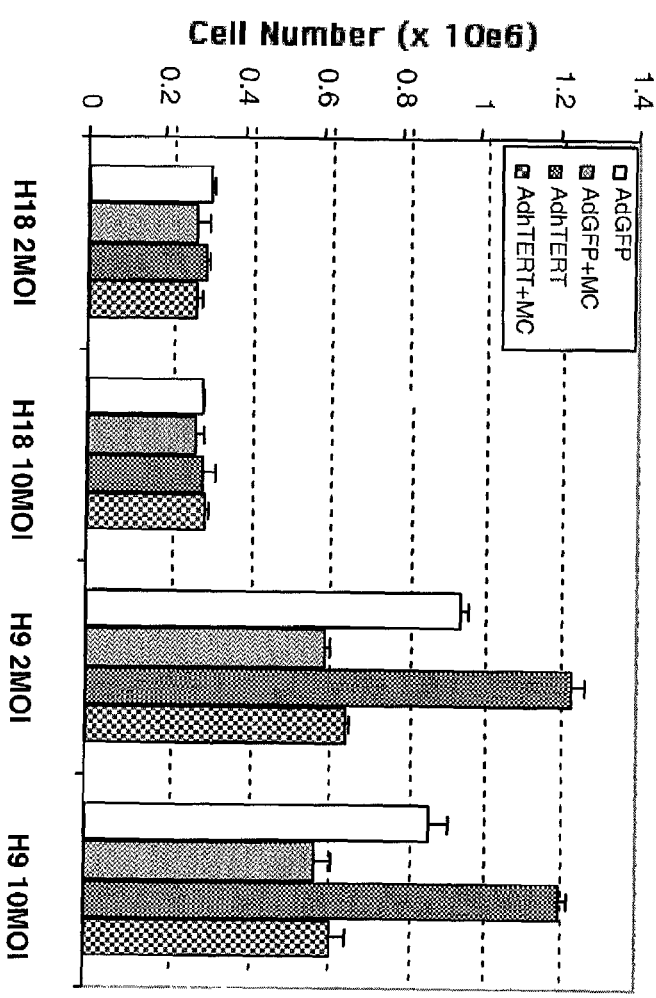

FIG. 10 shows results from an experiment in which migration of keratinocytes was uncoupled from cell proliferation. Neonatal keratinocytes from the HEKn9 line ("H9") proliferated after they were transduced to express telomerase (AdhTERT), or with vector control (AdGFP). In both cases, mitomycin c (MC) inhibited the proliferation by over 2-fold.

Figure 11:
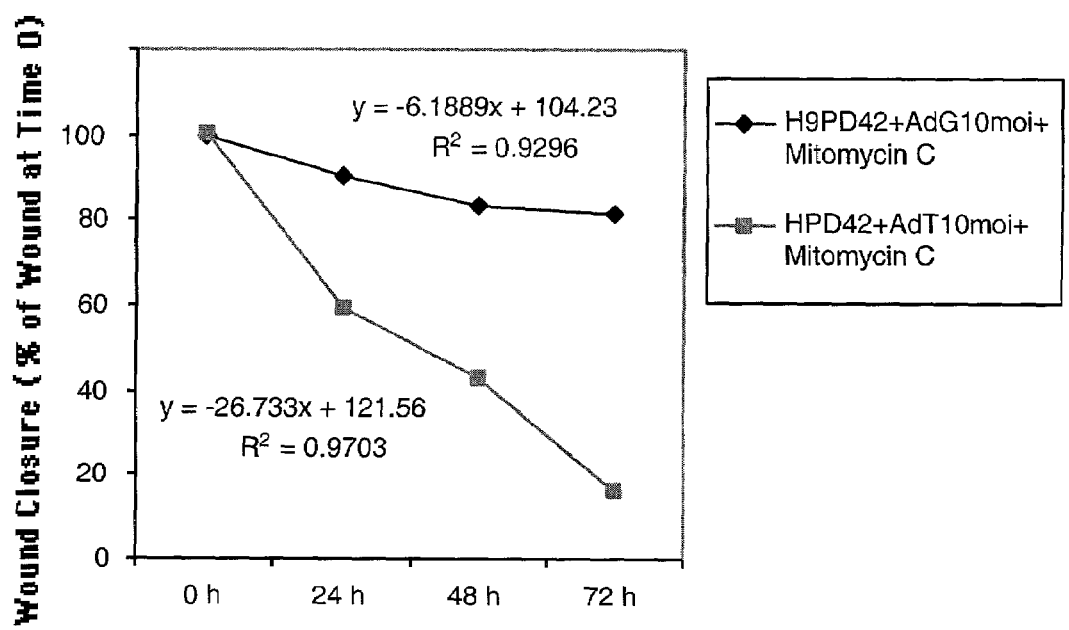

FIG. 11 shows the rate of wound closure in the presence of mitomycin c (10 µg/mL).

Figure 12:
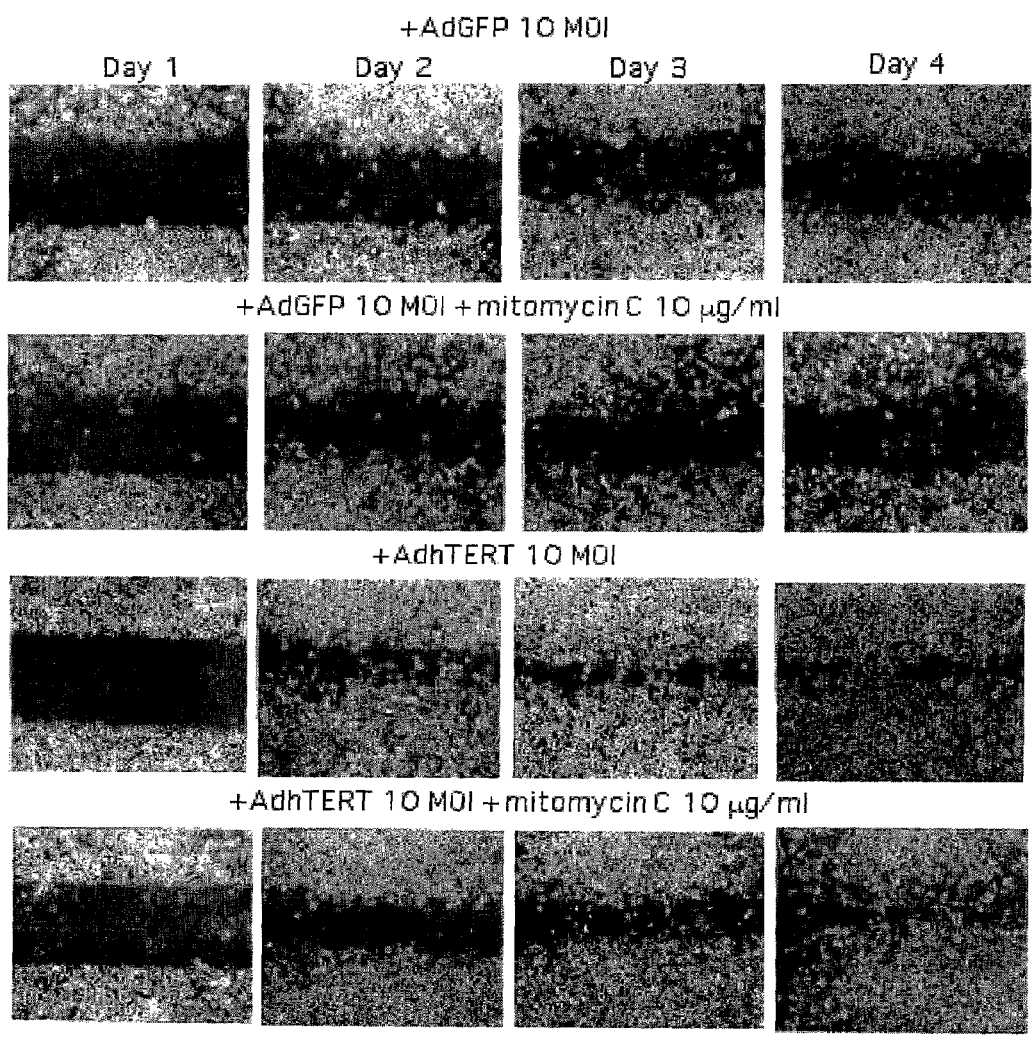

FIG. 12 shows the behaviour of keratinocytes in the wound healing model in the presence of mitomycin c. Telomerization of keratinocytes still increased the rate of wound closure by >3-fold, even though proliferation of the cells was inhibited by mitomycin c. This indicates that the enhanced wound closing induced by telomerase expression involves more rapid migration of the epithelial cells, independent from proliferative capacity of the cells.

Figure 13:
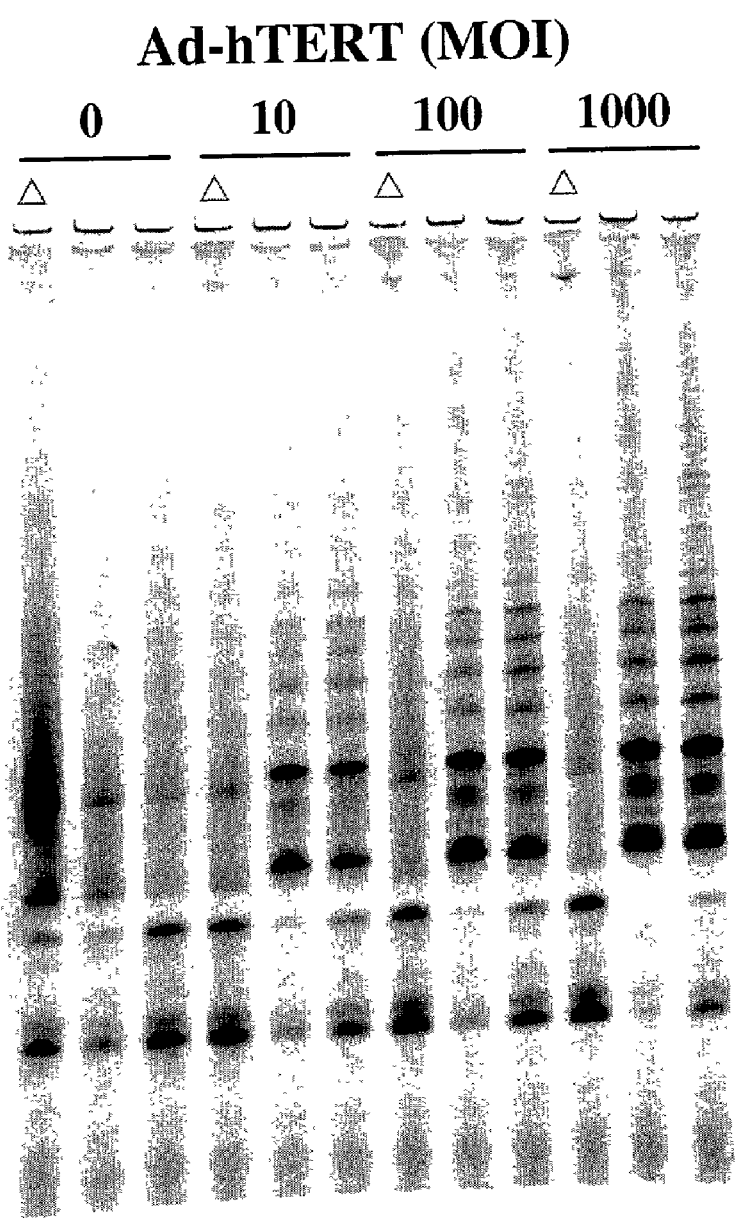

FIG. 13 shows reconstitution of telomerase activity in rabbit fibroblasts. Cultured fibroblasts were transduced with AdhTERT for 24 h, and then analyzed 48 h later for TRAP activity. Expression of the TERT gene reconstitutes telomerase activity in a dose-dependent manner.

Figure 14:
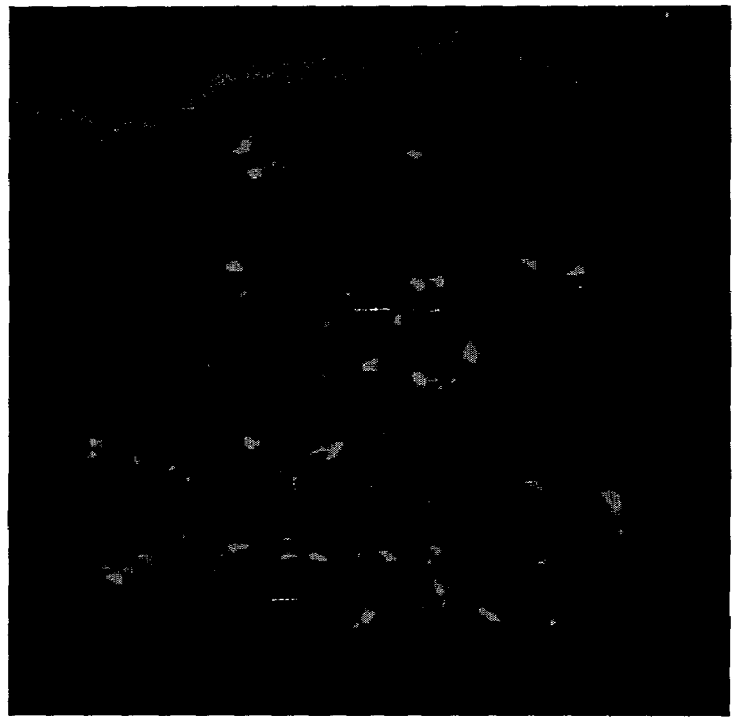
Figure 14:
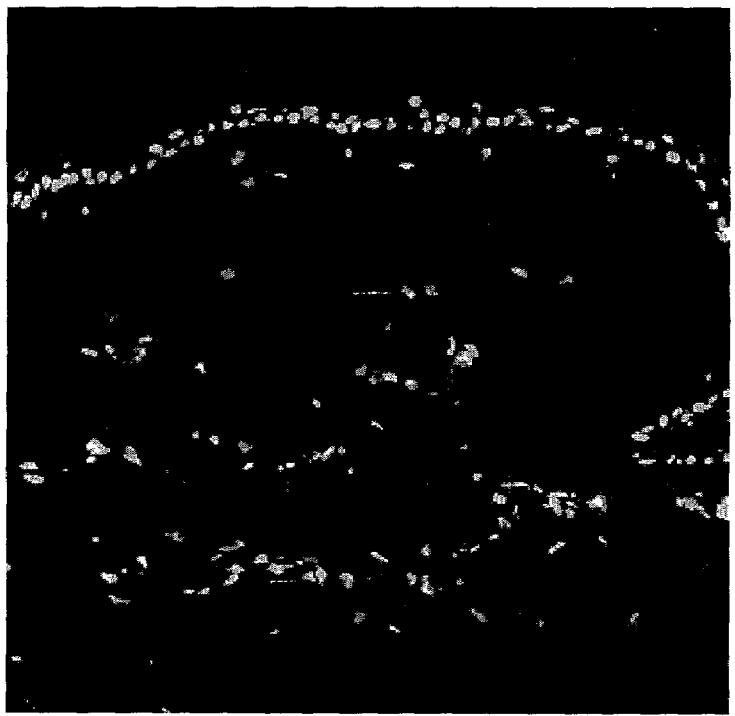

FIG. 14 shows hTERT gene transfer into rabbit skin tissues cultured ex vivo. An adenoviral vector encoding hTERT was injected intradermally and the tissues harvested 3 days later. Frozen tissues sections were stained with anti-hTERT antibody (top panel) and co-localized with nuclear staining using DAPI (bottom panel).

Figure 15:
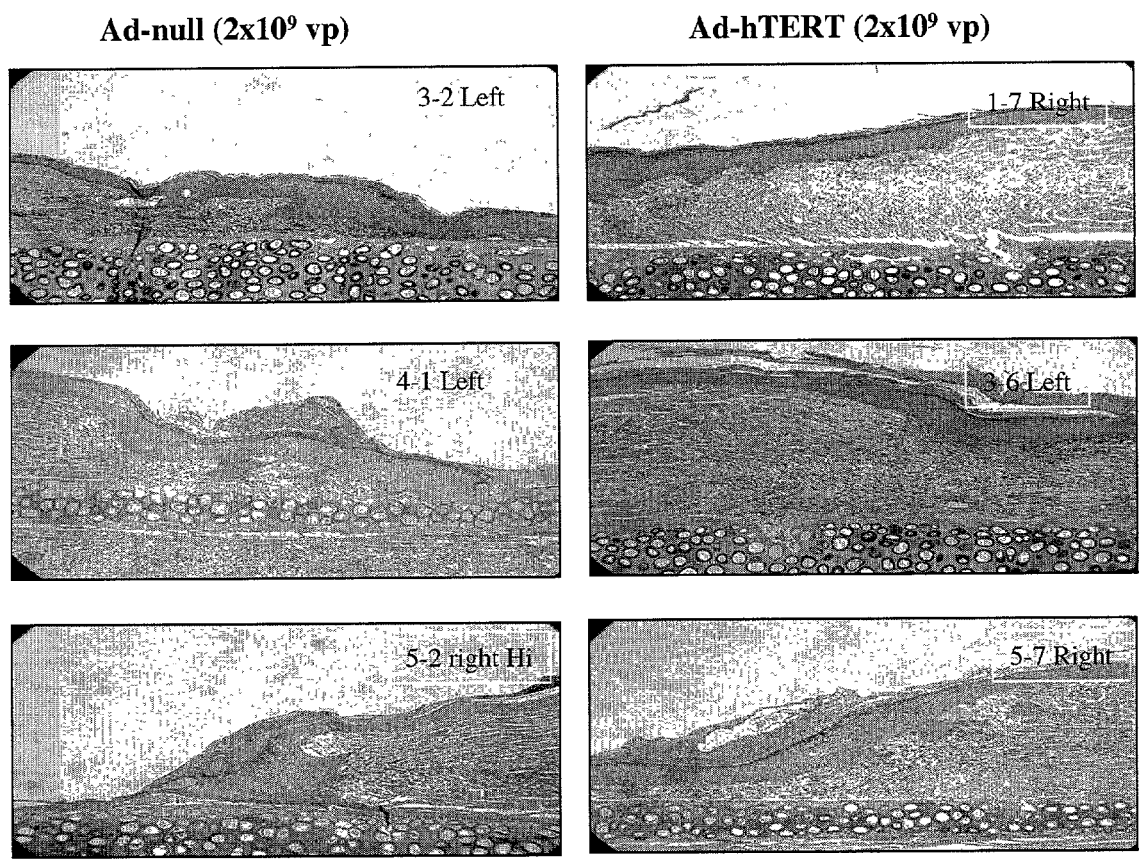

FIG. 15 shows paraffin sections from ischemic rabbit ear wounds treated with control vector (left) or adenovirus hTERT vector. The sections show increased formation of granulation tissue in the aged rabbit ear wounds treated with AdhTERT but not in the control.

Figure 16:
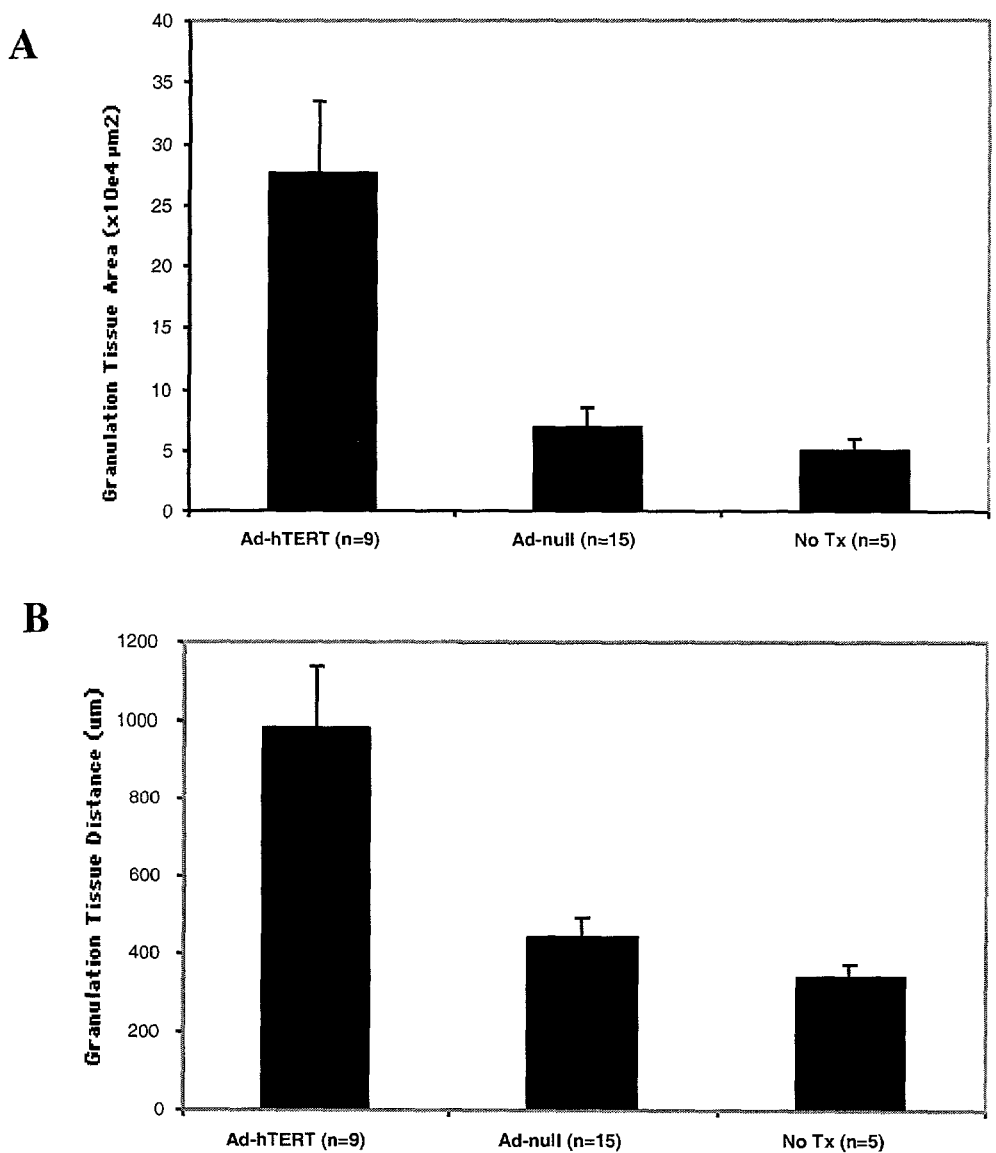

FIG. 16 quantitates the granulation tissue in aged rabbit ischemic wounds. The granulation tissue cross-sectional area (A) and distance migrated (B) was quantitated and expressed as mean values ±SEM. There was 3.9-fold increase in granulation tissue area (Panel A) and 2.2-fold increase in migration distance (Panel B) in the group treated with the AdhTERT vector, but not the control (p<0.01).

Figure 17:
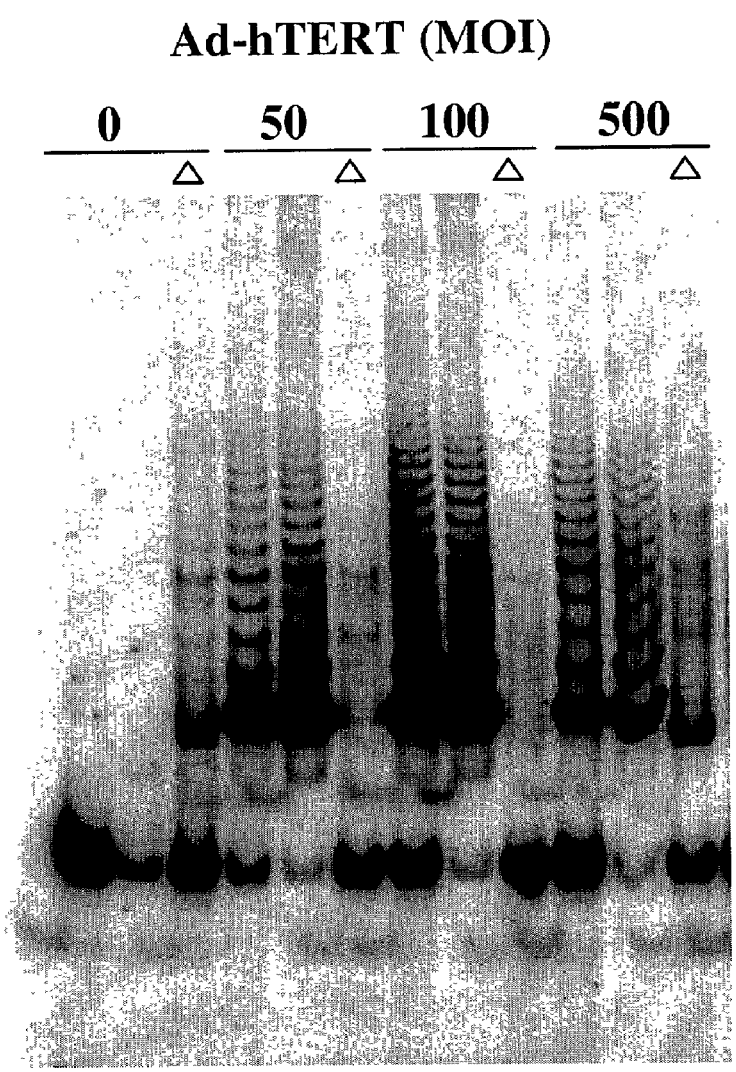

FIG. 17 shows AdhTERT reconstitution of telomerase activity in cultured rhesus monkey fibroblasts treated to express hTERT, as measured by TRAP assay.

Figure 18:
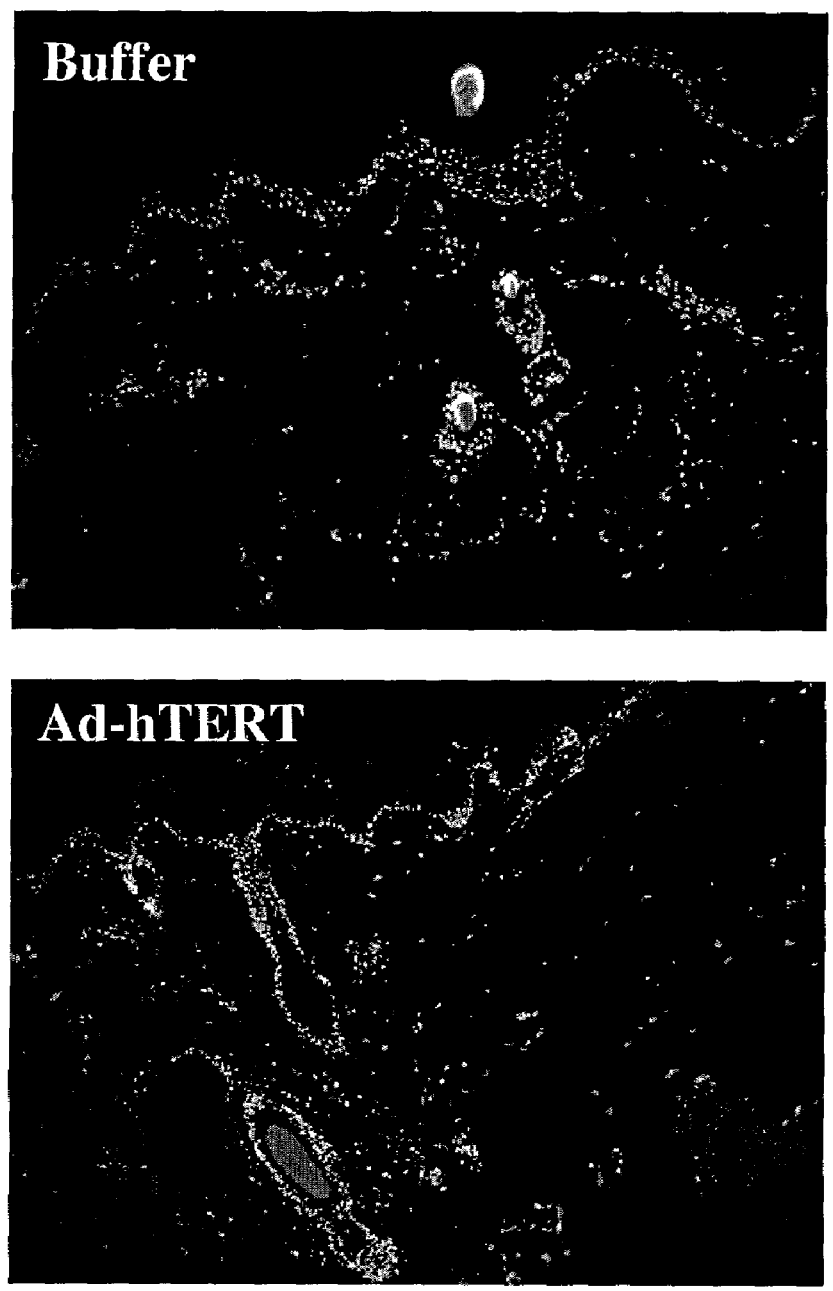

FIG. 18 shows efficient hTERT gene transfer into monkey skin. The tissue was obtained from aged rhesus monkey monkeys, and injected intradermally with buffer control (Top Panel), or AdhTERT (Bottom Panel). The panels show antibody staining for hTERT expression, co-localized with nuclear staining using DAPI. The results show that the vector caused hTERT protein expression in the dermal region.

No TRAP activity was detectable in AdhTERT transduced tissues, presumably due to low efficiency of gene transfer or expression.

Figure 19:
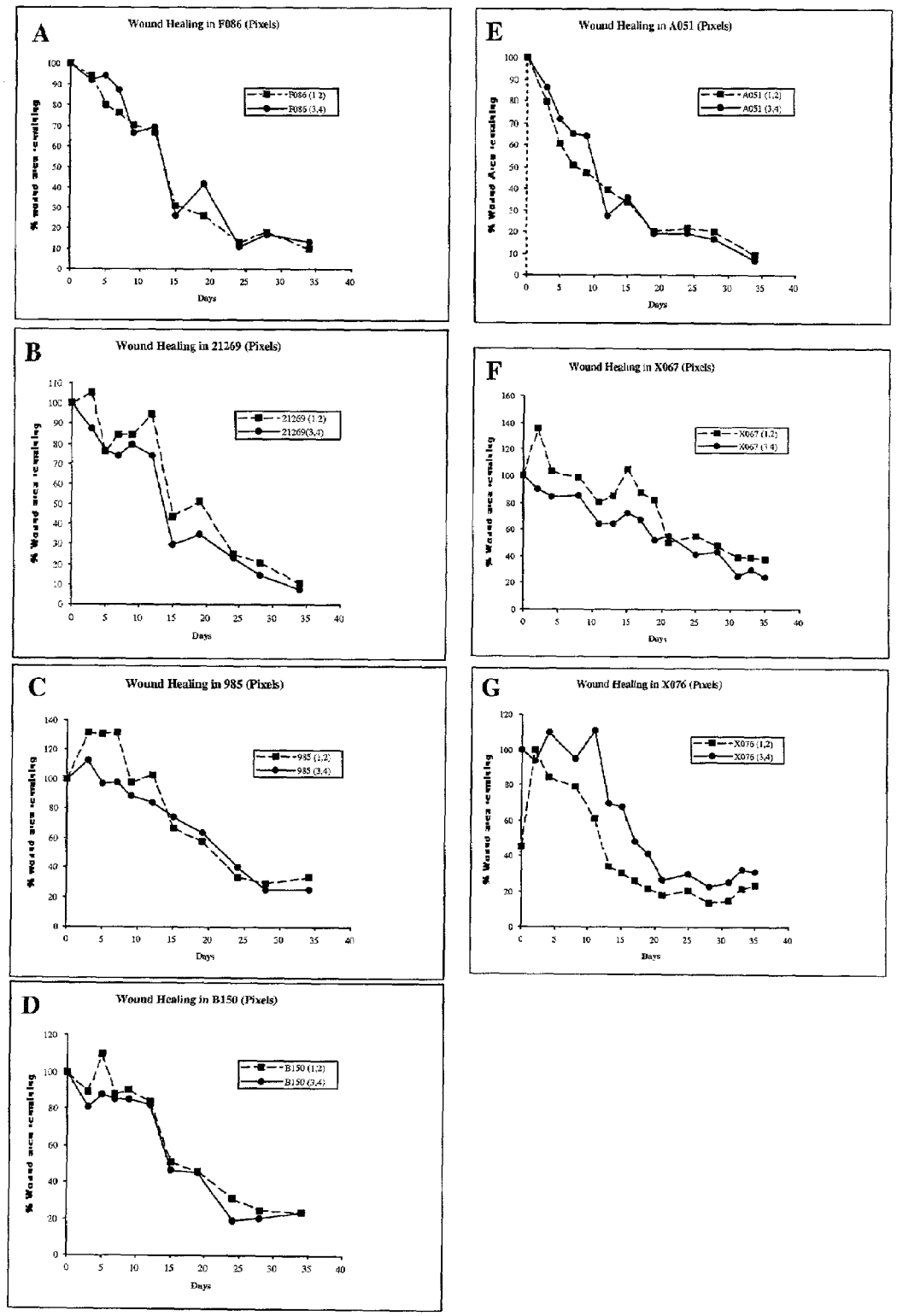

FIG. 19 shows wound closure in aged rhesus monkeys treated with AdhTERT (■) or control vector (●).

Figure 20:
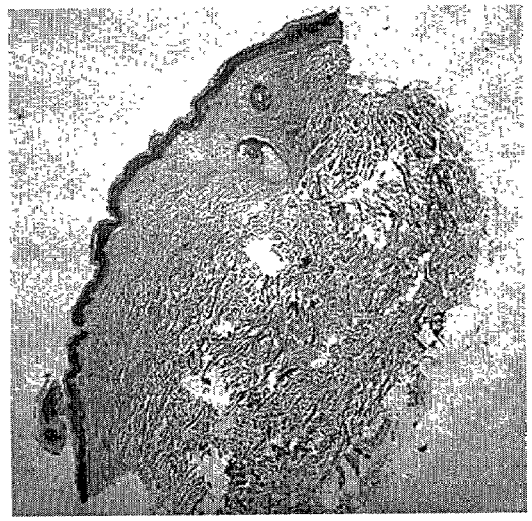
Figure 20:
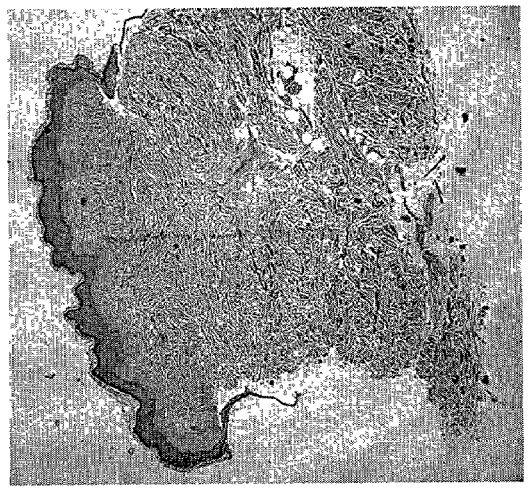
Figure 20:

FIG. 20 shows sections of normal human skin punches cultured ex vivo. The epidermal layer migrated along the cut edge of the punches with increasing time in culture.

Figure 21:
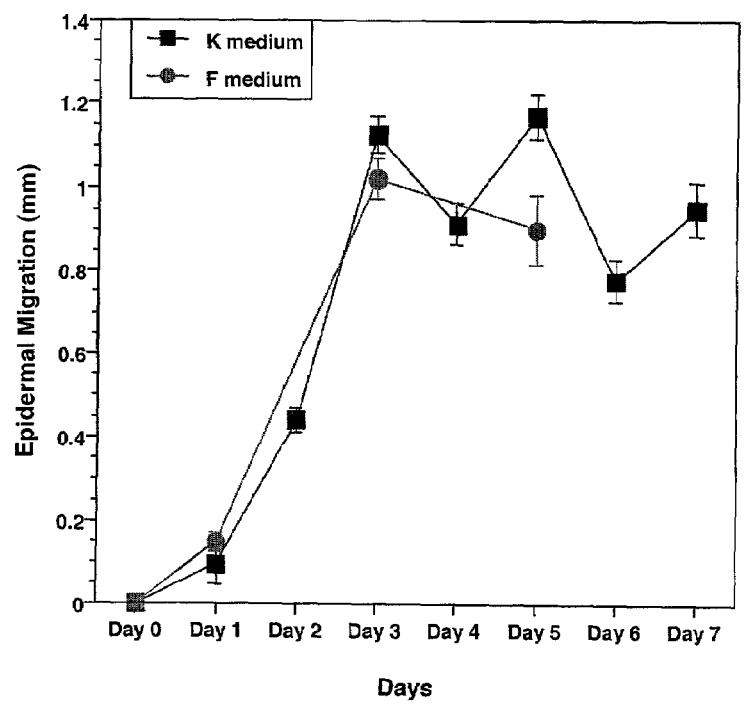
Figure 21:
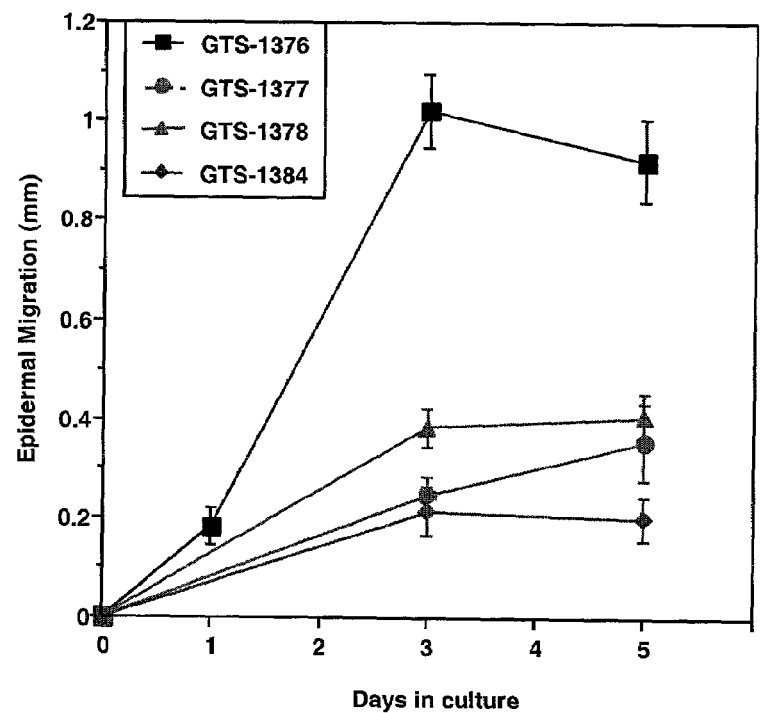

FIG. 21 (Top Panel) shows migration of epidermal cells in human skin punches cultured in different media. The Bottom Panel shows the pattern of epidermal migration for 4 normal human skin tissues over a period of 7 days. Epidermal migration rate was relatively consistent among punches obtained from the same donor.

Figure 22:
Figure 22:
Figure 22:
Figure 22:
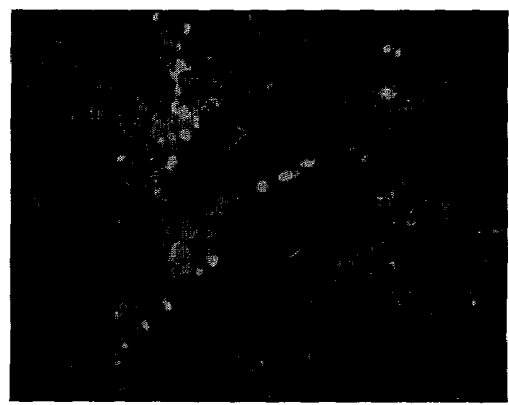

FIG. 22 shows expression of adenoviral delivery of hTERT to human skin punches. AdhTERT was injected into normal (left) or wound derived (right) skin punches. The cells were then stained with antibody for hTERT (upper panels), co-localized with propidium iodide (lower panels).

Figure 23:
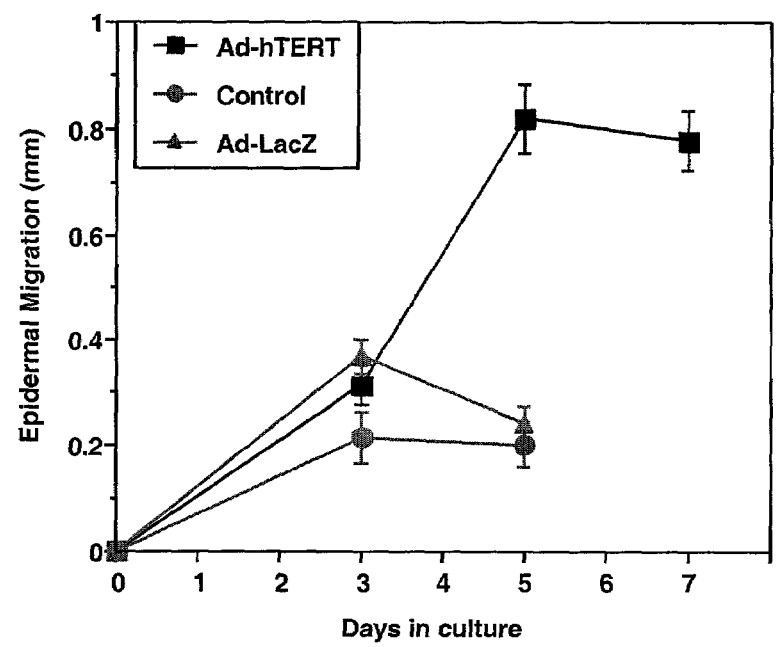
Figure 23:
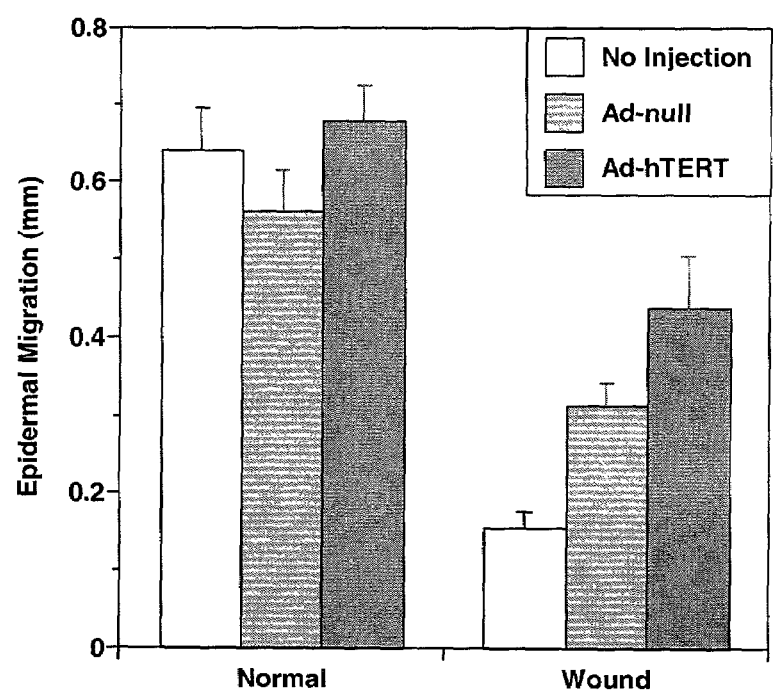

FIG. 23 shows that transient hTERT expression substantially enhances epidermal migration in human skin. The Top Panel provides results from a skin sample taken from a 78 year old donor. The epidermis of untreated skin punches or punches treated with AdLacZ (negative control) stopped migrating by 3 days. In contrast, the punch treated with AdhTERT migrated for 5 days to over twice the distance.

The Bottom Panel provides results of normal skin tissue, and skin taken near a chronic wound in the same donor (GTS 1388, age 39). Epidermal migration was slower in the wound. AdhTERT enhanced migration of the wound tissues by almost 3-fold, but had no effect on the normal tissue. The effect is greater than would be expected based on the number of cells detectably expressing hTERT, indicating that the transfected cells are recruiting activity in the surrounding epithelium.

DETAILED DESCRIPTION

The healing of an adult skin wound is a complex process, requiring collaboration between different cells and tissues. The phases of healing involve proliferation, migration, matrix synthesis, and contraction of the collaborating cells. Compositions that advance these processes may provide considerable improvement to the therapeutic modalities available.

It has now been discovered that increasing telomerase activity has a variety of effects that enhance the wound-healing potential of cells near the site of the wound. Replication is enhanced, and the cells become less susceptible to triggers of apoptosis. A surprising finding made in the course of this work is that telomerase expression also substantially enhances mobility of old cells surrounding the wound—allowing them to close the wound more rapidly. This is of considerable interest, because reepithelializing open areas of the wound creates a sterile barrier, and enhances healing of the subdermal tissues.

The enzyme telomerase is known to be generally involved in maintaining telomere length and forestalling replicative senescence in dividing cells. Most normal human somatic cells possess low or undetectable levels of telomerase, and their telomerase shorten with each cell division, ultimately leading to replicative senescence.

Kang et al. (Cell Growth Differ. 9:85, 1998) found that normal human oral keratinocytes (but not fibroblasts) have levels of telomerase measurable by telomeric repeat amplification protocol (TRAP) that diminished as the cells were passaged. Harle-Bachor et al. (Proc. Natl. Acad. Sci. USA 93:6476, 1996) dissected human skin taken during surgery, and tested for telomerase levels. They found that dermal fibroblasts were telomerase negative, but the epidermis had detectable telomerase activity, attributable to proliferative basal cells, which may act to promote regeneration of the epidermis. Fujimoto et al. (Oral. Oncol. 37:132, 2001) measured telomerase expression in oral keratinocytes and squamous cell carcinomas. Campisi et al. (J. Invest. Dermatol. 3: 1, 1998) and Mendez et al. (J. Vasc. Surg. 28:876, 1998) reported that loss of telomerase, proliferative capacity, and function are associated with skin aging and chronic wounds.

Artificially increasing the expression of telomerase can prevent the onset of senescence in some normal cells, increasing replicative capacity without causing malignant transformation (Bodnar et al., Science 279:349,1998; Yang et al., J. Biol. Chem. 274:26141, 1999; Morales et al., Nature Genet. 21:115, 1999). Ectopic expression of telomerase has been found to immortalize skin fibroblasts and microvascular endothelial cells, while maintaining growth control and differentiated function (Jiang et al., Nature Genet. 21:111, 1999). Farwell et al. (Am. J. Pathol. 156:1537, 2000) determined genetic and epigenetic changes in epithelial cells immortalized by telomerase. Yang et al. (Nat. Biotechnol. 19:219, 2001) determined the effect of telomerase on human microvasculature in vivo. Funk et al. (Exp. Cell Res. 258: 270, 2000) found that telomerase expression restores dermal integrity to in vitro aged fibroblasts in a reconstituted skin model.

However, before the filing of the present disclosure with the Patent Office, previous reports of epithelial cells with increased telomerase expression have taught against the invention claimed in this application. It has been reported that telomerase expression is insufficient to immortalize keratinocytes. Loss of cell cycle control was believed to be a second requirement for immortalization—specifically, inactivation of the pRb/p16$^{INK4a}$ pathway (Dickson et al., Mol. Cell. Biol. 20:1436, 2000; and Kiyono et al. Nature 396:84, 1998).

In spite of those discouraging reports, the experiments detailed below were conducted to determine what effect increased telomerase activity in keratinocytes would have on phenotypic features of the cells. Ectopic telomerase expression by itself was found to be sufficient for primary keratinocytes to bypass senescence and extend their life span—even in the absence of Rb/p16$^{INK4a}$ cell cycle control disruption. Normal levels of c-myc protooncogene expression, and normal growth and differentiation are maintained (Example 2, below). Furthermore, keratinocyte cultures established from adult donors and subsequently telomerized were shown to lose their susceptibility to apoptosis-inducing agents (Example 4).

A significant aspect of this discovery in the context of wound healing is that upon telomerization, epithelial cells from older adults acquire considerably improved capacity to mobilize and move into open areas of a wound. As shown in FIG. 6 (Example 3), keratinocytes transfected to express telomerase reverse transcriptase close a cleared 1 mm streak in tissue culture within 3 days—an improvement of at least 3-fold, compared with the vector control. The experiment described in Example 5 demonstrates that the increased mobilization is not simply due to increased proliferation rate: if the cells are treated with mitomycin c so as to block proliferation, wound closure still remains considerably enhanced.

Another remarkable finding during the course of this investigation is the ability of telomerized cells to recruit activity of other cells to promote wound closure. FIGS. 15 and 16 (Example 6) show that inducing telomerase activity at the site of a wound in animal models causes substantial increase in granulation tissue formed, expediting the healing process. FIG. 23 (Example 8) shows that telomerase preferentially affects senescent cells near the wound, causing them to revert to a younger phenotype, as illustrated by increased migration over the wound surface. The extent of improvement found in these experiments goes beyond what might be predicted from the number of cells actually expressing telomerase. The implication is that the telomerized cells secrete factors or otherwise influence neighboring cells to participate in healing.

The description that follows illustrates how this discovery can be implemented in clinical therapy in a variety of embodiments. Polynucleotide vectors and other agents can be applied to increase telomerase expression in cells around the site of a wound, thereby initiating or enhancing reepithelialization and closure of the wound over underlying tissues. Alternatively or in addition, the wound can be treated with a preparation of telomerized cells to overlay or repopulate the open area of a wound. These strategies can be implemented as effective treatments on their own, and can also be used as effective adjuncts to other wound-closing therapies.

General Techniques

For further elaboration of general techniques useful in the practice of this invention, the practitioner can refer to standard textbooks and reviews in cell and molecular biology, tissue culture, and veterinary and human medicine.

Methods in molecular genetics and genetic engineering are described generally in the current editions of *Molecular Cloning: A Laboratory Manual*, (Sambrook et al., Cold Spring Harbor); *Gene Transfer Vectors for Mammalian Cells* (Miller & Calos eds.); and *Current Protocols in Molecular Biology* (F. M. Ausubel et al. eds., Wiley & Sons). Cell biology, protein chemistry, and antibody techniques can be found in *Current Protocols in Protein Science* (J. E. Colligan et al. eds., Wiley & Sons); *Current Protocols in Cell Biology* (J. S. Bonifacino et al., Wiley & Sons) and *Current protocols in Immunology* (J. E. Colligan et al. eds., Wiley & Sons.). Reagents, cloning vectors, and kits for genetic manipulation referred to in this disclosure are available from commercial vendors such as BioRad, Stratagene, Invitrogen, and Clontech.

Cell culture methods are described generally in the current edition of *Culture of Animal Cells: A Manual of Basic Technique* (R. I. Freshney ed., Wiley & Sons); *Culture of Epithelial Cells* (R. I. Freshney ed., Wiley & Sons), *General Techniques of Cell Culture* (M. A. Harrison & I. F. Rae, Cambridge Univ. Press).

Topical publications include *Molecular Biology of the Skin: The Keratinocyte* (M. Darmon & M. Blumenberg, eds., Academic Press), *Wound Closure Biomaterials and Devices* (Chu et al. eds., CRC Press), and *Biomembranes Part V: Cellular and Subcellular Transport: Epithelial Cells* (S. Fleischer & B. Fleischer eds., Meth. Enzymol. vol. 191).

Cell Isolation

Skin cells and epithelial cells of various types can be isolated from tissue samples taken from humans and other species to validate the effectiveness of agents proposed for increasing telomerase levels, and to prepare some of the telomerized cell compositions of this invention.

Primary cultures of keratinocytes (skin epithelial cells) are readily obtained by culturing skin cells that have been separated by dissection and/or enzymatic digestion from a corresponding sample of epithelium, such as split-thickness explants of human skin. The cells can be passaged in serum-free medium, and form confluent, stratified cultures.

In one method, a layer of feeder cells is prepared form the 3T3 line of human fibroblasts (ATCC Accession No. CRL-1658). The feeders are grown in 3T3 medium at 37° C. to ~50% confluence, treated with mitomycin c (1-10 µg/mL) for 12 h, and then seeded at $2.5 \times 10^4$ cells/cm in keratinocyte growth medium (KGM: DMEM/F12 1:3, 10% fetal calf serum, 4 mM L-glutamine, 100 U/mL penicillin & streptomycin, 0.4 µg/mL hydrocortisone, cholera endotoxin (1×

$10^{-10}$ M), transferrin (5 µg/mL), liothyronine ($2\times10^{-11}$ M), adenine ($1.8\times10^{-4}$ M), insulin (5 µg/mL) and EGF (10 µg/mL). A skin sample is submerged briefly in alcohol 3 times, dried, and trimmed to remove hypodermis so only the epidermis and relatively dense dermis remain. The sample is then cut into 2-3 mm thin strips, and covered with medium containing dispase at 2 mg/mL overnight at 4° C., or for 2-4 h at 37° C. The epidermis is then peeled away from the dermis using two sterile hypodermic needles, and placed into 5 mL 0.05% trypsin solution with shaking for 1 min. Fifteen mL DMEM containing 10% FCS is added to inactivate the trypsin, and pieces of the upper epidermal layer is removed by passing through sterile gauze. The flow-through single-cell suspension is then centrifuged at 300 g for 5 min, resuspended in KGM, and plated on to the feeder layers at $2-5\times10^4$ viable cells cm$^{-2}$, or onto a collagen-IV coated flask.

Other methods for culturing keratinocytes are described by Rheinwald and Green (Cell 6:331, 1976), Flaxman et al. (Br. J. Dermatol. 92:305, 1975), Price et al. (J. Natl. Cancer Inst. 70:853, 1983), Wilke et al. (J. Natl. Cancer Inst. 80:1299, 1988), Germain et al. (Burns 19:99, 1993); and reviewed by Daniels et al. (Burns 22:35, 1996) and Barlow et al. (Methods Mol. Biol. 75:117, 1997). U.S. Pat. No. 5,712,163 provides chemically defined culture media for culturing epithelial cells, containing nutrients, insulin or IGF, transferrin or $Fe^{2+}$, $T_3$ or thyroxin, an ethanolamine, and calcium above 1.0 mM. Depending on the source and the culture method, doubling times can be achieved of up to 33 hours, and between 20 and 50 population doublings. Telomerase activity in the cultured epithelial cells can then be increased as described in the following section. U.S. Pat. No. 4,016,036 provides a process for serially culturing keratinocytes on a layer of inactivated fibroblast feeder cells. As an alternative, the cells can be grown on a porous analog of the extracellular matrix that supports the cells in vivo, such as collagen (Orgill et al., J. Biomed. Mater. Res. 15:39, 1998).

As an alternative, useful cell populations can be obtained by providing a population of stem cells, and then permitting or causing the cells to proliferate or differentiate into the desired phenotype. Li et al. (Proc. Natl. Acad. Sci. USA 31:3902, 1998) isolated and characterized candidate human keratinocyte stem cells. U.S. Pat. No. 6,200,806 (Thomson) and U.S. Pat. No. 6,090,622 (Gearhart et al.), and International Patent Publication WO 99/20741 (Geron Corporation) provide compositions of human pluripotent stem cells.

Tani et al. (Proc. Nati. Acad. Sci. USA 97:10960, 2000) provide enrichment methods for keratinocyte stem cells based on cell surface phenotype. Jones et al. (Cell 73:713, 1993) and International Patent Publication WO 99/47644 report enrichment of human keratinocyte stem cells to a high degree of purity using cell-surface integrins. Pellegrini et al. (Med. Biol. Eng. Comput. 36:778, 1998) provide cultivation conditions for human keratinocyte stem cells. Bata-Csorgo et al. (J. Clin. Invest. 95:317, 1995) report kinetics and regulation of human keratinocyte stem cell growth in short-term primary ex vivo culture.

Differentiation into a phenotype characteristic of certain types of epithelial cells can be determined according to characteristic morphology and cell-surface markers, such as cytokeratins (K1, K4, K10), integrins (integrin $\beta1$, $\alpha6\beta4$ integrin), and the receptor for keratinocyte growth factor. Stem cells differentiated to the desired phenotype can then be treated to increase the level of telomerase activity. Alternatively, the stem cell can be genetically altered to increase telomerase activity in cell progeny, and then differentiated into an epithelial cell with appropriate characteristics.

The compositions and techniques of this invention are generally applicable to different types of cells at the site of a wound, including but not limited to epithelial cells such as keratinocytes, and the underlying substrata. Reference to keratinocytes in the following description serves as a model for other types of cells, and is not meant to limit the practice of the invention except where explicitly required. Cells suitable for treatment in accordance with this invention include epithelial cells of the dermis, and of the internal mucosa. Clinical aspects of this invention can be performed on human patients, and veterinary subjects such as pets, livestock, other mammals, avians, and other vertebrates, as appropriate.

Other cells of interest in the practice of this invention can be studied in situ or isolated according to any suitable technique. For example, isolation and culture of human fibroblasts is described inter alia by Houck, Sharma & Hayflick, Proc. Soc. Exp. Biol. Med. 137:331, 1971; and in U.S. Pat. Nos. 5,460,959 and 6,093,393. Fibroblasts can be recognized by their characteristic stellate or spindle shape, ability to form collagen, or ability to respond to fibroblast growth factors (FGF). Gupta et al. (Exp. Cell Res. 230:244, 1997) and Cha et al. (Yonsei Med. J. 37:186, 1996) describe techniques for isolation and culture of human dermal microvascular endothelial cells. Isolation, characterization, and culture of mucosal epithelial cells are described by Pool-Zobel et al., Environ. Mol. Mutagen. 24:23, 1994; and in International Patent Publication WO 00/03002.

Increasing Telomerase Activity

Increasing telomerase activity in cells according to this invention can be accomplished by any effective mechanism, including but not limited to the following:

genetically altering the cell with a nucleic acid having an encoding region for telomerase reverse transcriptase (TERT);

artificially placing TERT protein or telomerase holoenzyme into the cell;

increasing TERT expression from the endogenous gene;

increasing the activity of endogenous TERT by applying an activating small molecule drug or other compound;

altering expression, availability, or activity of some other component involved in telomerase biology (such as telomerase RNA component or a telomere-associated protein), thereby effectively increasing telomerase activity; or any combination of these effects.

A convenient method to increase telomerase activity is to genetically alter the cells so that they express TERT, which is the limiting component of telomerase enzyme expression in most cells. A TERT gene can be cotransfected with a gene for the telomerase RNA component, or a TERT can be selected that is compatible with the RNA component already expressed by the cell. A cell is referred to in this disclosure as "telomerized", if it has been genetically altered with a recombinant polynucleotide to increase functional telomerase activity, either on a transient or permanent basis.

The polynucleotide and amino acid sequence of human TERT is provided in SEQ. ID NOs:1 & 2. See also Nakamura et al., Science 277:955, 199; and U.S. Pat. Nos. 6,166,178 and 6,261,836, which describe the use of TERT to increase replicative capacity of various cell types. Vectors used to express human TERT typically encode at least 10, 30, or 100 consecutive amino acids in SEQ. ID NO:2, or a protein sequence that is at least 70% or 90% identical to a fragment of SEQ. ID NO:2, and having telomerase reverse transcriptase activity. The encoding sequence typically encodes at least 25, 100, or 300 consecutive nucleotides in SEQ. ID NO:1, or a nucleotide sequence 70% or 90% identical to a fragment of SEQ. ID NO:1, or hybridizes to such a sequence under stringent conditions.

When TERT is referred to in this description, it is understood to mean a polypeptide comprising a TERT sequence from any species, with or without alterations (such as insertions, mutations and deletions) with respect to the native sequence—so long as the gene product has telomerase catalytic activity when associated with telomerase RNA component, as measured by TRAP assay, described below. Mouse TERT sequence is provided in International Patent Publication WO 99/27113. Other publications with telomerase-related sequences include International Patent Publication WO 98/21343 (Amgen); WO 98/37181 (Whitehead); WO 98/07838A1 (Mitsubishi); WO 99/01560 (Cambia), and U.S. Pat. No. 5,583,016 (Geron Corp.). U.S. Pat. Nos. 5,968,506 and 6,261,556 (Geron Corp.) describes purified mammalian telomerase and methods for obtaining it.

Expression vectors embodied in this invention are polynucleotides that have an encoding region, which upon expression in a target cell, is able to confer on that cell an increase in telomerase activity. Typically, vectors with a TERT encoding sequence will further comprise a heterologous transcription control element that will promote transcription in the intended undifferentiated or differentiated cell line. Sequences that can drive expression of the TERT coding region include viral LTRs, enhancers, and viral promoters (such as MPSV, SV40, MoLV, CMV, MSCV, HSV TK), eukaryotic promoters (such as β-actin, ubiquitin, elongation factors exemplified by Ef1α, ubiquitin, and PGK) or combinations thereof (for example, the CMV enhancer combined with the actin promoter).

Figure 1:
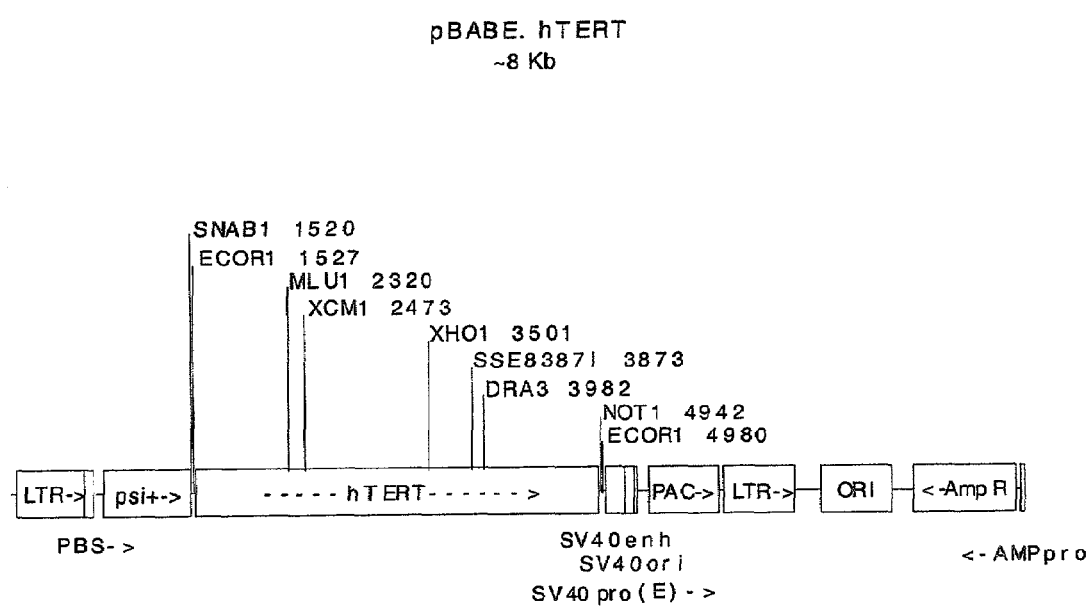
FIG. 1 is a map of the retroviral vector that was used to transduce keratinocytes for expression of telomerase reverse transcriptase (TERT). The human TERT encoding sequence and a puromycin drug selection gene (puro) is driven by a constitutive viral LTR promoter.

A TERT expression cassette can be delivered into the cell genome using a suitable vector system, such as a retrovirus or adenovirus. Transfection and expression of telomerase in human cells is described in Bodnar et al., Science 279:349, 1998 and Jiang et al., Nat. Genet. 21:111, 1999. For causing TERT expression on a permanent basis (for example, to create telomerized cells for administration), the pBABE retroviral vector shown in FIG. 1 is exemplary. For causing TERT expression on a transient basis (for example, for rejuvinating cells already present at a wound site), the AdhTERT adenoviral vector detailed in Example 4 is exemplary.

As an alternative, the replicative capacity of the cell line can be enhanced without integrating a TERT gene into the genome. For example, TERT can be transiently expressed using a suitable expression system such as adenovirus, or by introducing TERT protein (or the telomerase holoenzyme) directly into the cell. The TERT will be diluted out as the cell divides, but extension of telomerase in the parent cell should increase replicative capacity of the cell line by several doublings. Other suitable vectors include nucleic acid-lipid compositions effective for causing expression of the encoded protein, such as DNA lipofectin or lipofectamine complexes, neutral or anionic liposomes (U.S. Pat. Nos. 5,753,258, 5,756,122, 5,981,501), cationic lipid complexes (U.S. Pat. Nos. 6,008,202, 6,020,202 and 6,071,533), or combinations with amphipathic lipids (WO 00/59474).

Another alternative is to upregulate TERT expression from the endogenous gene by upregulating expression of trans-activating transcriptional regulators. The TERT promoter contains a number of regulator recognition sequences, such as c-myc, SP1, SRY, HNF-3β, HNF-5, TFIID-MBP, E2F and c-myb. See International Patent Publication WO 00/46355.

Another alternative is to deliver to the cell an enzyme capable of conferring telomerase activity. For example, telomerase can be purified by affinity techniques from cells that express the holoenzyme (U.S. Pat. No. 6,261,556). Telomerase reverse transcriptase (or an enzymatically active fragment) can be combined with telomerase RNA component (U.S. Pat. No. 5,837,857) either in solution or by cotranslation in a manner that permits reassembly into a telomerase holoenzyme. The active enzyme is then provided in a form that permits it to be translocated across the cell membrane (U.S. Pat. No. 5,059,532; WO 97/04748).

A further alternative is not to increase TERT expression, but enhance the effective activity of telomerase already present in the cell. This is effective in cells that have an endogenous level of TERT expression, such as in bone marrow progenitor cells and gonadal tissue. For example, TRF1 and TRF2 are proteins that bind to telomere repeats and regulate access of telomerase (Smogorzewska et al., Mol. Cell Biol. 20:1659, 2000). Decreasing expression of such factors may enhance the ability of telomerase to increase telomere length, thereby increasing replicative capacity of the cell. Furthermore, the presence of phosphatase inhibitors or protein kinase activators has been reported to increase telomerase activity (Li et al., J. Biol. Chem. 272:16729, 1998; Bodnar et al., Exp. Cell Res. 228:58, 1996).

Determining Telomerase Activity and the Effect on Cell Behavior

Evidence of increased telomerase expression can be obtained by a variety of techniques, including but not limited to determining gene transcript levels (for example, by Northern or RT-PCR analysis), protein expression (for example, by immunocytochemistry), or telomerase activity (for example, by primer extension assay). Extended lifespan or replicative capacity of the treated cells, while often desirable, need not be positively demonstrated for the invention to be put into practice, except where explicitly required.

Telomerase activity can be determined by TRAP assay (Kim et al., Science 266:2011, 1997; Weinrich et al., Nature Genetics 17:498, 1997), or other suitable technique (e.g., U.S. Pat. No. 5,741,677). Desirable levels of telomerase activity are at least 1, 4, 10, or 20 TPG units, calculated as described in Example 2. Evaluation of TERT expression by RT-PCR or immunoassay can be done by standard methods, using the sequences disclosed in U.S. Pat. No. 6,166,178. Absent of evidence to the contrary, it can be assumed that elevated levels of TERT transcript or protein corresponding to telomerase reverse transcriptase is an indication that the activity of telomerase in the cell is also elevated. The following assay kits are available commercially for research purposes: TRAPeze® XL Telomerase Detection Kit (Cat. s7707; Intergen Co., Purchase N.Y.); TeloTAGGG® Telomerase PCR ELISAplus (Cat. 2,013,89; Roche Diagnostics, Indianapolis Ind.); and LightCycler TeloTAGGG® human TERT quantification kit (Cat. 3,012,344).

Migration of isolated epithelial cells can be determined by plating or culturing in a monolayer, creating an adjacent free space on the substrate, and periodically observing cells moving into the free space. The migration occurs even in the absence of chemotactic factors, although the response of the cells to such factors may be of interest. The assay can also include a replication inhibitor such as mitomycin c, to decouple migration from cell replication. In a preferred method (Example 3), keratinocytes are grown as a monolayer on a standard tissue culture surface (such as a T25 flask) in regular medium until ~80-90% confluent. A transverse area is then cleared by scraping, and migration of the cells into the cleared area is observed as a function of time. Depending on other features of the cell, migration of telomerized epithelial cells can be 1, 2, 5, or 10 cell diameters per day; or 2, 3, or 5-fold higher than cells of the same type that are untreated or treated with a control vector.

Effectiveness of compositions of this invention in closing or reepithelializing a wound can be ascertained in a suitable model. Since hTERT affects telomerase activity in non-human primates and other mammals, preclinical development is well suited to animal testing. A number of established animal models are available. Jimenez et al. (J. Surg. Res. 81:238, 1999) measured the effect of KGF-2 in linear incisions made in dorsal skin of rats. Cribbs et al. (J. Burn Care Rehabil. 19:95, 1998) tested the wound healing effect of heparin-binding EGF-like growth factor in an animal burn model. Leivo et al. (Br. J. Dermatol. 143:991, 2000) measured reepithelialization rate and protein expression in a human suction-induced wound model.

Human skin can also be transplanted onto the nude mouse for evaluating wound healing in a superficial excisional full-thickness wound. See for example Rossio-Pasquier et al., Arch. Dermatol. Res. 291:591, 1999. Epidermal wound healing can also be characterized using human skin specimens in an organ culture model. Moll et al. (J. Invest. Dermatol. 111:251, 1998) found that dissociated autologous keratinocytes promoted reepithelialization of 3 mm diameter defects made in excised skin specimens.

Repopulation of human keratinocytes and fibroblasts can be tested in a spontaneous cell sorting model. See Funk et al., Exp. Cell Res. 258:270, 2000; and Wang et al., J. Invest. Dermatol. 114:674, 2000. Two-piece silicon chambers (Renner, Germany) are surgically implanted onto the backs of SCID mice to provide an aseptic wound bed resting on the muscle fascia. Dermal fibroblasts and keratinocytes are harvested from culture and resuspended in serum-free medium. Human skin reconstitutions are initiated by placing a slurry of $6 \times 10^6$ keratinocytes and $6-8 \times 10^6$ fibroblasts (isolated as already described, or obtained from an established cell line such as BJ fibroblasts). After one week, the upper chambers are removed to allow aeration of the skin surface. The skin can then be tested for blister resistance or examined microscopically.

A full-thickness human skin xenograft model can be set up using skin samples from tissue bank or surgical discards from hospitals. The samples are trimmed of subcutaneous fat tissue and cut into pieces of 1-2 $cm^2$. SCID mice are anesthetized using isofluorane, and 0.1 mL buprinex is administered s.c. (0.1 ml) behind the nape of neck as analgesic. A full thickness skin bed matching the size of the skin graft is created on the shaved dorsal region of the animal where there is a larger surface area and better vascular supply. One or two grafts are sutured in place using 4-0 Dermalon™ (Sherwood Davis & Geck) or 6-0 Vicryl™ (Ethicon). Any bleeding is stopped by applying gelfoam™. Petroleum jelly and telfa pad is applied, and the area bandaged using elastikon™ and conform™. The bandage and the sutures are removed 14 days later, with one change of bandage at 7 days. Scabbing ensues, and the grafts can be tested after the scabs come off, usually between 4-12 weeks.

The skin structure of the xenografts is monitored by immunohistochemistry using antibodies for human skin associated markers such as involucrin (NeoMarkers), associated with upper layers of the stratum corneum and the epidermis; collagen IV (Sigma), associated with the basal portion of the epidermis; and collagen I (Southern Biotech), associated with the dermal component. These antibodies are human-specific, and do not cross-react with murine skin. In general, the xenografts are positive for all three markers with some variability. The level of murine invasion can be determined using antibodies against human vs. mouse MHC Class I antigen. The amount of mouse cell invasion is variable from graft to graft, and increases with time post-surgery.

To monitor wound healing in the xenograft model, a 3 or 4 mm wound is created in the center of the skin xenograft using a sterile biopsy punch. Bleeding can be stopped using hemostatic sponges, and an occlusive bandage is placed on top of the wound for 2 days. Immediately before bandaging and every other day after bandage removal, the size of the wound is traced using an extra fine Sharpie® pen onto a clear, sterile Hybridwell™ strip until the wound is completely closed. Most of the wounds achieve complete closure by about 2 weeks. The size of the wound is quantified with respect to time by scanning each strip into ImageQuant™ or Photoshop™ 5.03, and performing area integration of the wound outlines with Openlab™ 2.1 or ImageQuant™. Using the best curve fit function, time to 50% and 75% wound closure is determined.

One way to determine the effect of increased telomerase expression is to deliver AdhTERT or control virus to the biopsy wound by direct intra-dermal injection, topical application, or both. For example, $1 \times 10^7$ to $5 \times 10^8$ particles are resuspended in 50 μL viral dilution buffer (saline +10% glycerol), and 10-15 μL aliquots are injected into 4 different sites i.d. using a tuberculin syringe with a 29 gauge needle. Alternatively, the virus is resuspended in 20 μL and directly applied to the wound bed. After allowing 30 minutes absorption and diffusion, the wound is bandaged using Opsite™ IV (Smith & Nephew) for 2-3 days. The kinetics of wound healing is then monitored as already described. The skin xenografts are harvested at different times following wounding for analysis of skin associated markers and telomerase expression.

Systems for testing telomerase activating agents and telomerized cells in tissue culture and animal models are illustrated below in Examples 2-8

Use of Telomerizing Agents and Telomerized Cell Preparations

The techniques and compositions provided in this disclosure can be used for a variety of desirable purposes. Such purposes include research or investigational work related to the behavior of epithelial cells or cells expressing telomerase. Of particular interest is clinical use in human or veterinary medicine, such as for the treatment of wounds or enhancement of properties of the dermis wherever desired.

Compositions for clinical use according to this invention include two categories: agents that can be used to increase telomerase activity in cells already present at or around an area of the epithelium in need of treatment; and compositions containing cells with increased telomerase activity. In general, such compositions are effective in treating a wound or otherwise enhancing properties of an epithelial surface in the body when applied individually, but they may also be used in combination where the benefits of both are desired.

Agents that Increase Telomerase Activity

Agents of this invention designed to increase telomerase activity or expression include vectors encoding TERT, agents that increase transcription of the endogenous TERT gene, and agents that affect the TERT gene product, transactivators or telomerase associated proteins in a manner that increases telomerase activity in cells near the wound that is being treated.

Compositions of this invention can be formulated for treating wounds of the skin or dermis, with or without involvement of the substratum and the underlying tissues. Compositions of this invention can also be formulated for treating wounds of other epidermal surfaces, including mucosal surfaces such as the bronchus, mouth, nose, esophagus, stomach, or intestine. Unless specifically required otherwise, the techniques and compositions of this embodiment are generally applicable to humans and other vertebrates.

Suitable TERT vectors include viral vectors, naked DNA, and DNA-liposome complexes, in which the TERT encoding region is operatively linked to transcription and translation elements active in the target cell. These vectors may include a constitutive promoter (such as the CMV or EF1α promoter), or a tissue-specific promoter (such as promoters for cytokeratins or integrins expressed in epithelial cells, or the receptor for keratinocyte growth factor).

When this disclosure refers to administration of an agent "to a wound site", what is meant is that the agent is placed at, in, or around the wound in one or more locations, such that cells at the site of administration are caused to express increased telomerase activity or increased expression of TERT. The type of cells that may be affected include epithelial cells, keratinocytes, microvascular cells, and other cells subjacent to the affected surface or exposed during wounding. It is understood that most agents of this invention administered with a view to increasing telomerase activity in a particular cell type, such as an epithelial cell, will inevitably also affect other cell types in the vicinity. Evidence of telomerase expression or clinical benefit in the general area of the wound is a desired object, and it is not necessary to understand the effect on a particular cell type at the treatment site in order to practice the invention.

The therapeutic composition will contain an amount of the agent effective for accomplishing one, two or more than two of the following effects: a) increase in the level of telomerase activity or TERT expression in epithelial cells at the treatment site; b) increase in the level of telomerase activity or TERT expression in fibroblasts or other cells at the treatment site; c) increase the mobility of epithelial cells on a solid surface (as determined in an in vitro assay); d) cause reepithelialization of a wound or epithelial surface; and e) increase the rate of wound closure or healing as determined by clinical criteria. These effects may be obtained in a single dose, or by sequential administration of two or more doses after an appropriate interval. The amount given per dose depends on the efficiency of the agent or vector chosen. For example, retroviral vectors are typically used at a titer of about $10^6$ to $10^7$ per mL, adjusted empirically.

General aspects of formulation and administration of pharmaceutical compounds can be found in the latest edition of *Remington's Pharmaceutical Sciences* (Maack Publishing Co, Easton Pa.). With respect to the use of nucleic acid vectors in therapeutic applications, the reader may wish to consult *The Skin and Gene Therapy* (U. R. Hengge & B. Volc-Platzer eds., Springer Verlag, 2000), or *Gene Therapy* (*Advances in Pharmacology*, Vol 40) (J. T. August, J. Coyle & M. W. Anders eds., Academic Press 1997).

The agent may be administered in an excipient suitable for topical administration, or administration to a wound site. This means that the excipient will have one or more of the following three properties: a) enhanced ability to penetrate the dermis or tissues at the wound site (compared with a neutral isotonic solvent); b) enhanced ability for keeping the agent at the site long enough to enhance the effect; or c) ability to prolong activity of the agent when administered to the dermis or the wound site. Excipients that enhance penetration contain organic solvents or additives such as alcohol, oils, glycols, and emoluments, or specific carriers that cause binding to the target cell. Excipients that keep the agent at the target site include creams, gels, and semisolid compositions, or solutes that produce a semisolid or high viscosity medium once applied. Excipients that prolong longevity of the agent after administration depend on the nature of the effective agent. For example, protein or virus compositions will persist longer on the skin or at a wound site if it is prepared in an excipient that contains protease inhibitors, such as metal chelators that inhibit metalloproteinase. Similarly, bare nucleic acid compositions will persist longer in an excipient that contains nuclease inhibitors. If helpful in enhancing the shelf life, the composition may be distributed in separate components to be combined just before administration.

The agent may alternatively or in addition be administered in a device suitable for topical administration, or administration to a wound site. Typically, the device will have the characteristic of either enhancing penetration or keeping the agent at the site long enough to enhance the effect. Devices of this nature include solid matrixes made of collagen, laminin, or other biocompatible polymers, and standard dressings (such as pads or bandages) made of gauze, nylon, or various plastics. The device is typically adapted to stay in place at the site of treatment by conforming to the shape of the site, and having fasteners or positions for accommodating fasteners that allow it to be attached to the site. The product may be distributed as a combined composition, in which the device is impregnated with the agent, and designed to deliver the agent upon attachment. Alternatively, the product may be distributed as a kit, comprising the therapeutically effective agent, and a device for preparing the treatment site, or for applying the agent to the treatment site, or for covering the site during or after treatment (such as a suitable dressing).

At the option of the manufacturer or distributor, the pharmaceutical composition may be packaged with (or marketed using) a written indication for use of the product in treating wounds or the epithelium according to the invention.

Telomerized Cell Compositions

Isolated cells with increased telomerase expression or activity can be assembled into a therapeutic composition in several different forms. Generally, the composition will contain telomerized epithelial and/or fibroblast cells matched to the species and type of wound being treated: for example, keratinocytes and fibroblasts for skin lesions; mucosal epithelial cells for lesions to the gastrointestinal tract. The cells may further be engineered to express other factors that promote wound healing, such as growth factors or cytokines (e.g., KGF or FGF).

In one embodiment, telomerized epithelial cells are prepared as a suspension in a pharmaceutically compatible excipient, such as a buffer or semi-solid gel. Siedler et al. (Arch. Dermatol. 136:676, 2000) propose human fibrin glue containing keratinocytes for healing of chronic ulcers. The epithelial cells are optionally accompanied by other cells that facilitate engraftment or support the cells after engraftment, such as fibroblasts, endothelial cells, or Langerhans cells, which may or may not be telomerized.

In another embodiment, the cells are attached to a solid carrier from which they can migrate once applied to the wound. Suitable carriers include microcarriers (particles of any shape less than 1000 microns in diameter, with particles in the 100 micron range being preferred), and made of a compatible matrix such as collagen. See Voigt et al. (Tissue Eng. 5:563, 1999) and LaFrance et al. (Tissue Eng. 5:153, 1999). The large surface-to-volume ratio of the microspheres can provide a vehicle for delivering appropriate cell numbers while minimizing the amount of biomaterial to be absorbed. The composition is then applied directly to the wound cavity or ulcer, or to the region surrounding the wound from which the cells can migrate.

In another embodiment, the cells are provided in the form of a flat sheet. This may be advantageous for providing more immediate protection, or treating areas that have a paucity of proliferation-competent endogenous epithelial cells. In general, the sheet will comprise a two-dimensional arrangement of epithelial cells, supported in some manner by a porous matrix produced by other cells, or manufactured artificially using a biocompatible polymer (such as collagen, laminin, or other matrix proteins). The epithelial cells may in some cases be underlaid by a supportive layer of cells such as fibroblasts that enhance engraftment or shelf life. In accordance with this invention, cells in the composition can be either telomerized before forming into sheets, or the sheet can be preformed ex vivo (or isolated from a donor), and then telomerized using one of the vectors described earlier. If fibroblasts are contained in the composition, they may also be telomerized. The sheet is then prepared for transport, and grafted onto the wound site in the clinic.

U.S. Pat. No. 4,304,866 describes a method of producing transplantable sheets by culturing keratinocytes in a vessel and then detaching a sheet of cells from the vessel with a neutral protease such as dispase. U.S. Pat. No. 5,759,830 provides a three-dimensional fibrous scaffold containing attached cells for producing vascularized tissue in vivo. Orgill et al. (J. Biomed. Mater. Res. 39:531, 1998) outline the use of island grafts of artificial skin, comprising keratinocytes and a copolymer of collagen and chondroitin sulfate. International Patent Publication WO 99/63051 outlines a bioengineered flat sheet graft prosthesis comprising layers of processed tissue material.

When this disclosure refers to administration of a cell composition "to a wound site", what is meant is that the composition is placed over, in, or around the wound, so as to provide coverage of at least part of the wound, or create a site from which the administered cells can migrate into the wound and promote closure or healing.

The cell compositions of this invention intended for clinical or veterinary use can be provided in an isotonic excipient, prepared under sufficiently sterile conditions for administration to the subject. They are optionally provided on a microparticle or matrix suitable for topical administration or administration to a wound site. This means that the microparticle or matrix is either adapted to adhere to the site of administration (using fasteners or dressing, if needed); or that the microparticle or matrix provides a vehicle from which the cells can migrate into the treatment site and participate in coverage of the site, reepithelialization, or healing.

Duration of the graft cells at the treatment site may be temporary or permanent, depending on the nature of the condition being treated and concurrent therapies. For permanent engraftment, it may be desirable to use compositions in which the cells are autologous or histocompatible with the patient being treated, although this is not always required. The product may be packaged as a single composition suitable for immediate use, or it may be packaged as a kit with component parts in separate containers to be admixed before administration, or for sequential administration. The kit may also contain a dressing or other substance for covering the site or improving engraftment. At the option of the manufacturer or distributor, the pharmaceutical composition may be packaged with (or marketed using) a written indication for use of the product in treating wounds or the epithelium wherever needed.

Conditions Suitable for Treatment

The techniques and compositions of this invention may be used for the treatment of wounds or other conditions of the epidermis wherever desired.

Some of the medical conditions that can be treated according to this invention are acute conditions (such as lesions suffered in trauma, burns, abrasions, surgical incisions, donor graft sites, and lesions caused by infectious agents). Other medical conditions that can be treated are chronic conditions (such as chronic venous ulcer, diabetic ulcer, compression ulcer, pressure sores, and ulcers or sores of the mucosal surface). Included are skin or epithelial surface lesions caused by a persistent inflammatory condition or infection, or by a genetic defect (such as keloid formation and coagulation abnormalities). This invention also contemplates manipulation of the skin and repair of any perceived defects in the skin surface for other purposes, such as cosmetic enhancement.

In the usual course of therapy, the treatment site is monitored for response to treatment. Desirable effects for agents that increase telomerase expression or activity include cell proliferation or migration at the treatment site, epithelialization of the surface, closure of a wound if present, or restoration of normal physiological function. Throughout this disclosure, "epithelialization" or "reepithelialization" of a treatment site means that the site acquires an increased density of epithelial cells as a result of the therapy that is applied.

Desirable effects for cell compositions include coverage of the treatment site, survival of the engrafted cells, lack of immune rejection, closure of the wound if present, or restoration of normal physiological function. The engrafted cells may participate in wound closure either by participating directly in the healing process (for example, becoming part of the healed tissue), or by covering the wound and thereby providing an environment that promotes healing by host cells.

Ultimate choice of the treatment protocol, dose, and monitoring is the responsibility of the managing clinician.

Other Uses of the Invention

Isolated cells, compositions, and mixed cell populations of this invention can also be used for any other desirable research, developmental, or therapeutic purpose. The high proliferative capacity and high mobility of telomerized epithelial cells can be maintained as the cells are passaged in culture, thereby providing a standardized reservoir of cells for further investigation. Cell cultures or matrixes can be combined with a putative therapeutic or cosmetic agent, and any alteration in cell viability, proliferation, migration, or other phenotypic feature can be correlated with efficacy of the agent. Telomerized cells can also be used in living wound models such as those described earlier, to screen the ability of other compounds to promote cell migration or the process of reepithelialization.

The examples that follow are provided by way of further illustration, and are not meant to limit the claimed invention.

EXAMPLES

Example 1

Telomerization of Keratinocytes

To determine the effect of telomerase on human keratinocytes, early passage (<PD5) cultures of both neonatal and adult keratinocytes were grown in an optimized medium and transfected with a vector encoding human telomerase reverse transcriptase (hTERT).

Human primary epidermal keratinocytes were obtained from Cascade Biologics (Portland, Oreg.). The cell lines are referred to in this disclosure according to their Cascade lot designation: HEKa18, HEKa2, HEKn9 and HEKn4 are two lines of adult keratinocytes and two lines of neonatal keratinocytes.

The cells were cultured in EpiLife™ serum-free medium plus calcium chloride at 0.06 mM and Human Keratinocyte Growth Supplement (HKGS) (Cascade Biologics, Portland, Oreg.). Cells were plated at $2-4\times10^5$ cells per T75 flask, refed every 2-3 days, and subcultured 4-7 days before high cell density was reached. PD (the number of population doublings) for every passage was calculated as $\log_2$ (number of cells at time of subculture/number of cells plated). Cumulative PD was plotted against time in culture so that replicative life span, senescence, slow growth or crisis, and immortalization could be assessed. Cells were considered to have been immortalized when the life span of a culture was greater than 50 PDs beyond that of parental cell line, and growth curves showed no sign of a decrease in proliferation rate.

FIG. 1 is a map of the amphotrophic retroviral vector that was used to transduce cells for expression of telomerase reverse transcriptase. The hTERT encoding sequence and a puromycin drug selection gene (puro) is driven by a constitutive viral LTR promoter (Nakamura et al., Science 277:955, 1997). Control cultures were infected with an equivalent vector without hTERT. Viral titers were determined by the infection of NIH-3T3 cells with BABE-puro-hTERT or control BABE-puro vectors, and were typically $3-5\times10^6$/mL.

Figure 2:
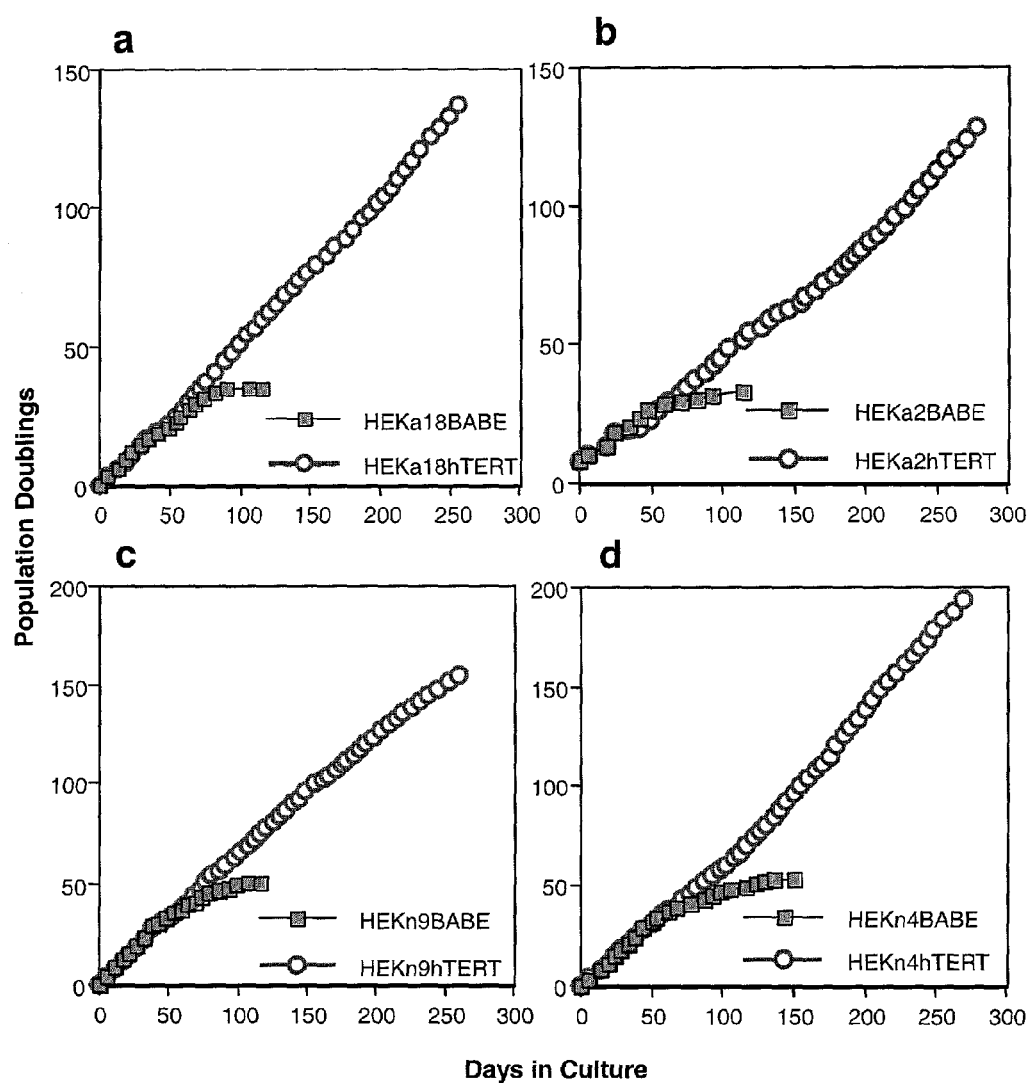
FIG. 2 shows that TERT expression increases replicative capacity of primary human keratinocytes. Culture of adult keratinocytes (HEKa18, HEKa2) and neonatal keratinocytes (HEKn9, HEKn4) were transduced with control or TERT expression retroviral vectors, drug selected, and then serially passaged as shown.

FIG. 2 shows proliferation potential of control and hTERT-expressing human primary keratinocytes. Early life span cultures of two adult keratinocyte lines (HEKa18, HEKa2) and neonatal lines (HEKn9, HEKn4) were transduced with control (BABE) or hTERT expression retroviral vectors, drug selected, and then serially passaged.

Control HEKa and HEKn cultures senesced at PD 33-38 and PD51-56 respectively, as evidenced by complete cessation of cell division, senescence-associated (SA) β-galactosidase positive staining, and enlarged cellular morphology. In contrast, hTERT-transduced keratinocytes had indefinite lifespans and were negative for SA-β-galactosidase staining. Moreover, all hTERT-keratinocytes exhibited no slow phase growth or crisis stage, during which clonal populations with pRb/p16$^{ink4a}$ inactivation could have emerged

Example 2

Characterization of Telomerized Cells

Total RNA was isolated from keratinocytes using High Pure™ RNA Isolation Kit (Roche). 100 ng total RNA was used for real time PCR quantitation of hTERT and hTR (the telomerase RNA component) with a light cycler (Roche). TeloTAGGG™ hTERT and hTR quantitation kits (Roche) and PCR were used according to the manufacturer's protocol. Telomerase activity was assessed by the PCR-based telomeric repeat amplification protocol (TRAP) assay (Kim et al., Nucl. Acids Res. 25:13, 1997). Mean telomere restriction fragment (TRF) lengths were determined by Southern blotting (Bodnar et al., Science 279:349, 1998).

FIG. 3 shows the effect of hTERT transduction on hTERT expression, telomerase activity and telomere dynamics in keratinocytes. Panel (a) shows quantitation of hTERT transcripts in four lines of hTERT transduced keratinocytes (transcripts per 100 ng RNA$\times10^{-6}$). Panel (b) shows telomerase activity in the hTERT transduced keratinocytes at various population doublings. Cell lysate equivalent to 100 cells was used for each lane. The H1299 tumor cell line is a positive control. HT=reaction mixture heat treated before PCR; IC=internal control. Panel (c) shows terminal restriction fragment lengths of keratinocytes transduced with hTERT or control vector (BABE).

Telomerase activity was quantitated using the formula $$TPG=100\times[(TP-TP')/TI]/[(R8-B)/RI]$$

where TP is telomerase products from test sample, TP' is products from heat-inactivated control, TI is internal control of sample, R8 is products from quantification standard, B is buffer blank, and RI is internal control of standard. The total product generated (TPG) is defined as 0.001 amol (600 molecules) of primer TS extended for at least three telomeric repeats by telomerase in the sample. One TPG corresponds roughly to the telomerase activity in one immortal cell. Values obtained are shown in Table 1:

TABLE 1

Telomerase Activity in hTERT-Transduced Keratinocytes

| Sample | TPG Value |
| --- | --- |
| HEKa18h TERT-PD23 | 5.6 |
| HEKa18h TERT-PD71 | 7.2 |
| HEKa9h TERT-PD18 | 16 |
| HEKa9h TERT-PD90 | 10.4 |
| H1299 (control) | 4.5 |

The transduced keratinocytes expressed relatively high levels of hTERT transcripts that increased with passage, likely reflecting enrichment of telomerase-expressing cells (Panel A). This level of expression is roughly 100-200 fold greater than that seen in tumor cell lines such as H1299 and Raji. Expression of hTR (the RNA subunit of telomerase) was steady and similar between hTERT-keratinocytes and vector controls (data not shown). hTERT-keratinocytes had high levels of telomerase activity and elongated telomerase, while control keratinocytes were telomerase negative and telomerase progressively shortened with passage (Panels B & C).

pRb phosphorylation is required for progression through the S phase. pRb activity is regulated by proteins such as CDK4, cyclin D1 and p16 (Weinberg et al., Cell 81:323, 1995). To determine whether there were perturbations in the pRb/p16 pathway in hTERT-transduced keratinocytes, expression of pRb and p16 proteins was analyzed by Western blot analysis.

Western analysis for p16 (G175-1239, PharMingen), pRb (G3-245, PharMingen), p53 (OP29, Oncogene), cyclin D1 (G124-326, PharMingen), CDK4 (DCS-35, PharMingen), c-myc (N-262, Santa Cruz Biotechnology), GADD45 (H-165, Santa Cruz Biotechnology) and TFIIB (SC-225, Santa Cruz Biotechnology) was performed as described in Wang et al. (Nature 405:755, 2000). The antibody to pRb recognizes both hyper- and hypo-phosphorylated forms of the proteins (Jiang et al., *Nature Genet* 21:111, 1999).

FIG. 4 shows the expression of cell cycle regulation proteins and c-myc in hTERT-keratinocytes.

(a) Vector control (BABE) and hTERT-expressing keratinocytes were maintained at either subconfluent cultures (S) or confluent cultures for 72 hours (C) and analyzed for pRb, p53, cyclin D1, CDK4, and TFIIB.

(b) Vector control and hTERT-expressing keratinocytes were analyzed for $p16^{INK4a}$ protein levels at early and late population doublings (PDs). (c) Vector control (B) and hTERT-keratinocytes at different PDs were analyzed for c-myc and GADD45 expression. TFIIB protein was used to normalize loading in panels (b) and (c).

It was found that pRb was predominantly hyperphosphorylated in subconfluent, proliferating keratinocytes, but was hypophosphorylated when the cells were maintained at confluence (Panel A). Levels of pRb were also down-regulated at confluence. Cyclin D1 and CDK4 were expressed at similar levels in proliferating hTERT-transduced and control keratinocytes, but cyclin D1 expression was down-regulated upon growth arrest (Panel a). The amount of p16 increased in late passage keratinocytes (Panel b). In contrast to previous reports, it was found that all hTERT-keratinocytes retained stable $p16^{INK4a}$ protein levels even after dramatic life span extension (Panel b).

p53 plays an important role in initiation of senescence-associated growth arrest (Sedivy et al., Proc. Natl. Acad. Sci. USA 95:9078, 1998). In these experiments, it was found that p53 was normally expressed in hTERT-transduced keratinocytes in both growing and non-growing states (Panel A). Thus, neither $pRb/p16^{INK4a}$ nor p53 inactivation are required for immortalization of human keratinocytes by telomerase.

Wang et al. (Nature 405:755, 2000) reported that hTERT-driven cell proliferation and immortalization are associated with activation of the c-myc protooncogene. This was after long-term culture of immortalized epithelial cells that had suffered previous inactivation of the $pRb/p16^{INK4a}$ pathway. However, it has now been discovered that hTERT-immortalized normal keratinocytes at both early and late passages, show that c-myc and GADD45 (a downstream target of c-myc) were expressed at levels similar to that seen in control populations (FIG. 3, Panel C).

Telomerase-transduced cultures were examined under conditions known to induce arrest and differentiation of young keratinocytes: high cell density, high calcium concentrations, EGF removal, TGF-β treatment, or exposure to phorbol ester.

FIG. 5 shows long-term retention of normal keratinocyte growth control mechanism by keratinocytes transduced with the hTERT retroviral vector ("T", first 4 series), or vector control ("B", next 2 series). SCC-4 is a squamous cancer cell line (positive control). Cells were plated at low density in EpiLife™ medium, either in the presence or absence of EGF; or in the presence or absence of 12-O-tetra-decanoylphorbol-13acetate (TPA). Cells were counted 7-8 days later, and growth rate under these conditions was determined (average ±S.D of three experiments).

Under these conditions, the fractions of cycling hTERT-keratinocytes were similar to that of control cells. In contrast, the SCC-4 human squamous cell carcinoma cell line was not dependent on EGF or inhibited by phorbol ester. These results indicate that hTERT-immortalized keratinocytes retain normal c-myc expression and growth regulatory mechanisms.

Example 3

Telomerized Cells Close Wounds More Rapidly

Human keratinocyte migration and proliferation are essential for re-epithelialization of skin wounds. In this experiment, the effect of replicative senescence and hTERT-transduction in a culture model of wound closure was examined.

Keratinocytes were plated at $1 \times 10^5$ cells/T25 flask. Once the cells reached 80-90% confluence, the monolayer of cells was scratched in a standardized manner with a plastic apparatus to create a cell-free zone approximately 1 mm across.

Retrovirus transduction for permanent expression was effected using the hTERT/BABE vector described in Example 1. When the keratinocytes were growing in log phase, the medium was replaced with 5 mL viral supernatant in DMEM/F12 medium at a titer of $3-5 \times 10^6$ mL$^{-1}$. After culturing overnight at 37° C. in 5%$CO_2$/95%, the cells were washed twice in PBS, and selected for 7 days in EpiLife™ medium containing 0.5 μg/mL puromycin, and then grown in regular EpiLife™ medium.

Adenovirus transduction was effecting using a replication-deficient (E1 and E3 deleted) adenovirus, containing an expression cassette in which the hTERT encoding region is under control of CAG (CMV enhancer, chicken β-actin promoter, and the rabbit β-globin polyadenylation signal). When the keratinocytes were ~80-90% confluent, the well was scratched to create a cell-free zone, and simultaneously transduced with the adenovirus vector at 2-10 MOI in EpiLife™ medium (1 MOI≡1 PFU≡0.7 TCID). The cells were cultured overnight at 37° C. in 5%$CO_2$/95%, washed twice in PBS, and then grown in regular EpiLife™ medium.

In vitro re-epithelialization or wound closure was documented by photography through a 40×objective over a 1-4 day period. The width of the wound was measured at three different places in each of three replicate plates, and the rate of wound closure was calculated by linear regression of the mean wound width as a function of time.

FIG. 6, Panel (a) shows results of transduction for TERT expression using the retroviral vector. When measured by the time required to produce a 50% wound closure ($T_{50}$), it was found that young keratinocytes (PD8) closed culture wounds at a rate roughly 3-fold faster ($T_{50}=33\pm1.2$ h) than that seen with old keratinocytes (PD41) ($T_{50}=113\pm5.7$ h, p<0.00002). Stable hTERT expressing keratinocytes transduced at early passage, on the other hand, retained their youthful rates of wound closure ($T_{50}=32\pm0.8$ hr, p<0.0002), even at very late passages (PD152).

To test whether telomerase could rescue age-associated deficits in wound closure in this model system, late-passage cultures of keratinocytes were wounded and then transduced with adenoviral vector for transient hTERT expression (AdhTERT). The identical adenovirus containing GFP in place of hTERT was used as a control.

FIG. 6, Panel (b) shows the results of transduction with the adenovirus vector. Old keratinocytes were efficiently infected with adenovirus since 60-70% of cells were positive for expression 7 days after infection with AdGFP at 10 MOI and high levels of telomerase activity were seen when AdhTERT was used (data not shown). Short-term hTERT expression in late passage keratinocytes (PD42) remarkably accelerated wound healing in vitro, as shown by a near-complete wound closure on day 4 in AdhTERT-treated ($T_{50}=34\pm2.3$ h) but not AdGFP-treated keratinocytes ($T_{50}=109\pm17.7$ h, p<0.001). The rate of closure of the transient hTERT transduced cultures was similar to that of young cells.

FIG. 7 shows the rate of wound closure over the 4 days following transduction for increased expression of TERT, or with a control vector. Either long-term expression (resulting from retrovirus transduction) or transient expression (resulting from adenovirus transduction) caused a comparable acceleration in wound healing over the 4-day period.

Example 4

Telomerized Cells are Resistant to Apoptosis

Cells transduced with the hTERT retrovirus were measured for their resistance to apoptotic cell death, induced by TNF-α or UV irradiation.

Apoptosis is characterized in the early stages by translocation of membrane phosphatidylserine (PS) from the inner to the outer leaflet of the plasma membrane. Annexin V is a 35-36 kDa calcium-dependent binding protein with a high affinity for PS, which can be used to stain for externalized PS in early apoptosis.

For TNF-α induced apoptosis, keratinocytes were transduced with hTERT retrovirus or BABE control. The transduced cells were then cultured for 48 hours in standard keratinocyte culture medium, or medium containing TNF-α. The cells were washed in PBS containing 0.5% BSA (or 1% FBS). $5\times10^5$ cells were combined with 0.5 mL 1×Binding Buffer from the Annexin V FITC Kit. 5 µL Annexin V FITC and 10 µL propidium iodide were added, and the mixture was incubated at room temperature in the dark for 10 min. They were then measured for percentage positive cells and mean fluorescence intensity by flow cytometry.

FIG. 8 shows the results. Adult keratinocytes treated with vector control (HEKa2 BABE PD22) were ~20% susceptible to apoptotic cell death, which increased in the presence of TNF-α. However, only ~10% (<2-fold less) of the telomerized keratinocytes (HEKa2 hTERT PD25) showed evidence of apoptosis, and were resistant to the effects of TNF-α.

For apoptosis induced by UV irradiation, primary adult keratinocytes were seeded in 100 mm TC dishes at $3\times10^5$ per dish, and cultured in EpiLife® medium. Cells reached about 40% confluence at 3 days, and were transduced in fresh medium containing AdhTERT at 10 MOI. AdhTERT is a replication-deficient, E1 and E3 regions deleted, adenovirus containing a cassette encoding the human telomerase gene under the control of CAG (comprising the CMV enhancer, chicken actin promoter, and a portion of 3' untranslated region containing the polyadenylation site of rabbit globin gene). After culturing with AdhTERT for 72 h, the cells were washed twice with $Ca^{++}$- and $Mg^{++}$-free PBS. UV irradiation was performed for 24 h, and the cells were then stained with Annexin V.

FIG. 9 (Top) shows the results of this experiment. Transfection with the hTERT adenovirus vector protected the keratinocytes against UV-induced irradiation at doses up to 10 mJ cm$^{-1}$.

FIG. 9 (Bottom) shows that the protective effect of hTERT is retained as the cells divide. In this experiment, cells were transfected with the AdhTERT for 3 days at 40% confluence, and then cultured under conditions that allow cell proliferation. On day 8 (when the cells were 75% confluent), they were subject to UV irradiation for 24 h, and then washed and stained the next day.

The results show that the protective effects of hTERT extend to the progeny of the cells transfected on day 8. Since adenovirus vectors provide only transient expression, the long-lasting effect may ensue from the lengthening of telomerase caused by hTERT in the parent cells.

Example 5

Enhanced Wound Closure by Telomerized Cells Does not Depend on Cell Relication

In the previous examples, telomerase expression was shown to increase replicative capacity of keratinocytes, render them less susceptible to apoptosis, and increase their capacity to re-epithelialize a wound. In this experiment, the wound healing effect was decoupled from the proliferation effect, showing that wound closure is not due simply to an increase in cell replication.

Keratinocyte cell lines were plated at $1\times10^5$ per T25 flask. Once they had grown to 80-90% confluence ($\sim5\times10^5$), the cell monolayer was scratched as before to create a cell-free zone. The cells were treated with mitomycin c at 10 µg/mL for 2 hours. The medium was then aspirated and replaced with fresh EpiLife™ medium, with or without Adeno-hTERT or Adeno-GFP (control), to transiently increase telomerase expression. After transducing overnight, the medium was replaced with fresh medium, and the rate of wound closure was measured for 4 days in triplicate.

FIG. 10 shows the effect of mitomycin c (MC) on cell proliferation. The cells were trypsinized and counted on day 4 to determine the extent of proliferation since mitomycin c treatment. The HEKa18 line ("H18") was at PD37 when plated in this experiment. This is near the full extent of its normal replicative capacity (FIG. 2). Accordingly, little further proliferation was observed, regardless of whether mitomycin c was present. The HEKn9 line ("H9") was at PD42 when plated, which is below its full replicative capacity (FIG. 2). This cell line proliferated through several doublings when cultured in regular medium. However, mitomycin c reduced the proliferation rate by well over 50%.

FIGS. 11 & 12 show the effect of mitomycin c (10 µg/mL) on cell migration of HEKn9 keratinocytes transduced to express hTERT ("AdT"), compared with vector control ("AdG"). The transient expression of hTERT accelerated wound closure by over 3-fold, even in the presence of mitomycin c.

A summary of the kinetics of epithelial cell migration is shown in Table 2.

TABLE 2

Kinetics of Wound Closure

| Sample | $T_{50}$ (hours to achieve 50% wound closure) |
| --- | --- |
| HEKn9 pBABE PD8 | 33.0 ± 1.2 |
| HEKn9 pBABE PD41 | 113.4 ± 5.7 |
| HEKn9 PD42 + AdGFP | 108.9 ± 17.7 |
| HEKn9 PD42 + AdGFP + Mitomycin c | 189.2 ± 28.9 |
| HEKn9 pBABE/TERT PD152 | 31.6 ± 0.8 |
| HEKn9 PD42 + AdhTERT | 34.3 ± 2.3 |
| HEKn9 PD42 + AdhTERT + Mitomycin c | 40.3 ± 2.1 | pBABE = retrovirus control
pBABE/TERT = retroviral vector for expressing TERT
AdGFP = adenoviral vector for expressing GFP (control)
AdhTERT = adenoviral vector for expressing TERT In conclusion, it has been found that hTERT-treated keratinocytes have increased replicative capacity, and are resistant to apoptosis. They retain normal growth control, as shown by dependence on epidermal growth factor (EGF) and sensitivity to phorbol ester (TPA). hTERT-treated keratinocytes do not spontaneously activate c-myc, and retain functional p53 and pRB/p16$^{ink4a}$ cell cycle checkpoint. Both stable and transient hTERT expression increases migration and accelerates wound healing in aging keratinocytes.

Example 6

Enhanced Wound Healing Using hTERT in the Aged Rabbit Ischemic Ear Model

In this study, it was shown that AdhTERT gene delivery induces a specific and robust enhancement of granulation tissue formation in the ischemic ear wounds of aged rabbits.

Methods

The adenovirus vector encoding hTERT under control of the CAG expression system was described in Example 4. Rabbit fibroblasts were obtained from ATCC (CRL-1414), grown in BME +10% FBS to passage 33, infected with AdhTERT or Ad-null for 24 hr at different MOI, and analyzed 48 hrs later for telomerase activity using the TRAP assay. Skin tissues were obtained from young rabbits and maintained in DMEM +10% FBS ex vivo. The tissues were injected intradermally with 2×10$^9$ viral particles and harvested 3 days later. Frozen tissue sections were analyzed for hTERT expression using anti-hTERT antibody as described below.

Ear wounds were induced in rabbits as an established clinically relevant model for wound ischemia (Ahn, S. T. & T. A. Mustoe, Ann Plast Surg 24:17, 1990; Wu et al., Am J Pathol 154:301, 1999). New Zealand white rabbits (>55 months of age) were prepared by shaving the ears and prepping with betadine solution. An incision was made to the level of bare cartilage at the base of each ear. Both ears of each rabbit were made ischemic by dissecting the rostral and central arteries, with preservation of the caudal, central and rostral veins. The incision was closed with a running 4-0 Vicryl™ suture. Three to five full thickness (6 mm) circular wounds were then made on the inner surface of the ear down to bare cartilage.

Adenoviral gene transfection was performed by delivering 2×10$^9$ viral particles of AdhTERT or Ad-null (control) per ear wound. Two thirds of total dose was injected at 4 periwound locations at 5 µL each, using a Hamilton syringe with a 30 gauge needle. One third of the dose was topically placed within the defect in 10 µL. Sterile Tegaderm™ dressing (3M Health Care, St. Paul, Minn.) was placed over each wound upon completion of the procedure. The dressings were changed as needed over the next 12 days, at which time the animals were sacrificed and the wounds harvested for histological and biochemical analysis.

Telomerase activity was measured according to standard TRAP assay procedures described earlier, as applied to frozen skin tissue homogenized in lysis buffer.

Immunohistochemical analysis of hTERT expression was performed on 6 µm frozen tissue sections fixed in 4% paraformaldehyde in PBS (pH 7), rinsed in PBS and permeabilized in PBS containing 0.1% Triton™ X-100. The sections were blocked in 5% goat serum in PBS for 30 min at room temp, drained and incubated with anti-hTERT antibody (1A4, 2.5 µg/ml) for 1 h. After washing several times in PBS, Texas-Red™ conjugated goat anti-mouse IgG (Jackson Immunolabs, Westgrove, Pa.) was added at 7.5 µg/mL for 30 min at room temp in the dark. The sections were then washed again with PBS, mounted using Vectashield™ mounting medium containing DAPI (Vector Labs), and viewed under a Nikon fluorescent microscope.

Data were collected from histological sections to determine the extent of wound re-epithelialization and new granulation tissue formation. The wound healing parameters were measured twice using a calibrated reticle from H&E-stained paraffin tissue sections by observers blinded to treatment. Analysis of all wound parameters was performed by Student's t-test and analysis of variance with post hoc analysis using Tukey's standardized range. All comparisons were made to paired wounds. Any dependent associations were analyzed using Spearman's correlation of coefficients.

Results

FIG. 13 shows reconstitution of telomerase activity in rabbit fibroblasts, which do not express detectable endogenous telomerase. Cultured fibroblasts were transduced with AdhTERT at 0, 10, 100 or 1000 MOI for 24 h, and then analyzed 48 h later for TRAP activity. For each group, 4000 and 40,000 cell equivalents were loaded in the first and second lane, respectively. The triangle denotes lysates (40,000 cells) that were heat-inactivated prior to assay. AdhTERT but not Ad-null (the control vector) was effective in reconstituting telomerase activity in a dose-dependent fashion. Subsequent immunocytochemical analysis also showed hTERT positive cells in AdhTERT transduced rabbit fibroblast cultures.

FIG. 14 shows hTERT gene transfer into rabbit skin tissues cultured ex vivo. AdhTERT or Ad-null was injected intradermally and the tissues harvested 3 days later. Frozen tissues sections were stained with anti-hTERT antibody (red fluorescence, top panel) and co-localized with nuclear staining using DAPI (blue fluorescence, bottom panel). hTERT protein was expressed mostly in the dermal region. However, no TRAP activity was detectable in AdhTERT transduced tissues, most likely due to the low efficiency of gene transfer/expression.

To determine if hTERT expression in rabbit skin can enhance wound healing, AdhTERT or Ad-null was administered to ischemic ear wounds of aged rabbits by both intradermal injection and topical application. Pilot experiments using young rabbits showed that AdhTERT causes hTERT expression in the dermal regions 3 days after wounding and virus administration . Analysis of the aged wounds at day 12 also showed hTERT positive dermal cells, albeit at less frequency, probably due to the transient nature of adenoviral gene expression.

FIG. 15 shows H&E stained paraffin sections from ischemic rabbit ear wounds treated with Ad-null (left) or AdhTERT (right) and harvested on day 12. There was a dramatic increase in granulation tissue formation in the aged rabbit ear wounds treated with AdhTERT, but not in wounds treated with Ad-null. Table 3 summarizes the quantitative data.

TABLE 3

Histological analysis of aged rabbit isohemic ear wounds

| Wound parameters (day 12 post-wounding) | No Treatment (n = 5) | Ad-null (n = 15) | AdhTERT (n = 9) |
|---|---|---|---|
| Granulation tissue | | | |
| Area (×10$^4$ μm$^2$) | 5 ± 1 | 7 ± 2 | 27 ± 6* |
| Distance (μm) | 340 ± 5 | 445 ± 45 | 986 ± 152* |
| Peak to peak distance (μm) | 5245 ± 180 | 5048 ± 102 | 3890 ± 330* |
| Peak height (μm) | 335 ± 28 | 312 ± 27 | 407 ± 20 |
| Epithelial tissue | | | |
| Epithelial gap (μm) | 2750 ± 822 | 1529 ± 468 | 1167 ± 519 |
| Epithelial height (μm) | 145 ± 23 | 124 ± 14 | 130 ± 18 |

*p < 0.01 between Ad-null and AdhTERT

FIG. 16 shows granulation tissue formation in aged rabbit ischemic wounds. Ischemic rabbit ear wounds were treated with Ad-null, AdhTERT or no treatment and then harvested 12 days later. The granulation tissue cross-sectional area (A) and distance migrated (B) was quantitated and expressed as mean values ±SEM. There was 3.9-fold increase in granulation tissue area and 2.2-fold increase in migration distance in the AdhTERT treated group relative to the Ad-null or no treatment group (p<0.01). However, no difference was observed in the growth or migration of the overlying epithelium.

The results show that transient expression of hTERT can specifically enhance new granulation tissue formation, which is critical in effecting wound healing. The lack of observable effect on epithelial growth or migration is most likely due to the inefficient gene delivery to the epithelium.

The hTERT effect on granulation tissue formation is quite dramatic, despite the relative inefficient gene transfer to the skin. This suggests that in addition to influencing the phenotype and/or replicative capacity of the transduced cells, hTERT expression cells may indirectly influence the phenotype of neighboring cells—for example, by elaborating trans-acting factors or altering the extra-cellular matrix environment. There was no abnormal inflammatory response in the hTERT treated wounds beyond that observed with normal wound healing, suggesting that local AdhTERT gene delivery can be used safely.

Example 7

Wound Healing in Aged Rhesus Monkey Monkeys

The ability of hTERT gene to reconstitute function in rhesus monkey cells was demonstrated by positive hTERT protein expression and telomerase activity following AdhTERT transduction of rhesus monkey fibroblasts in culture.

FIG. 17 shows AdhTERT reconstitution of telomerase activity in culture. Rhesus monkey lung fibroblasts (NIA AG11856A) were grown in DMEM +10% FBS to population doubling 8.3, infected, transduced with AdhTERT at 0, 50, 100 or 500 MOI for 24 hrs and then analyzed 48 hrs later for TRAP activity. For each group, 1000 and 5000 cell equivalents were loaded in the first two lanes, respectively. The triangle denotes lysates (5,000 cells) that were heat-inactivated prior to assay.

The results show that monkey skin fibroblasts do not express detectable endogenous telomerase activity. The weak signals in the heat inactivated lanes are likely to be due to leakage from other adjacent lanes. Upon transduction with AdhTERT but not Ad-null, telomerase activity was reconstituted and the level of telomerase activity showed a dose related increase with the transducing viral dose. Immunocytochemical analysis also revealed hTERT positive cells in AdhTERT transduced rhesus monkey fibroblast cultures.

FIG. 18 shows the efficiency of hTERT gene transfer into monkey skin. The tissue was obtained from aged rhesus monkeys and maintained in DEME +10% FBS ex vivo. The tissues were injected intradermally with buffer control (Top Panel), or AdhTERT (2×10$^9$ viral particles, Bottom Panel) and harvested 3 days later. The panels show antibody staining for hTERT expression, co-localized with nuclear staining using DAPI (Example 6). The results show that AdhTERT caused hTERT protein expression in the tissue, mostly in the dermal region. No TRAP activity was detectable in AdhTERT transduced tissues, presumably due to low efficiency of gene transfer or expression.

Wound healing experiments were conducted using an established model in aged rhesus monkeys (Roth et al., J Gerontol A Biol. Sci. Med. Sci. 52:B98-102, 1997). Full thickness wounds were created in female rhesus monkey monkeys (18-32 years old) anesthetized with ketamine (15 mg/kg) and diazepam (1 mg/kg). Four separate 5 mm punch biopsy wounds were made on the dorsal side of the animals. AdhTERT or Ad-null virus was applied at 10$^{10}$ viral particles per wound to two wounds at the time of wounding. To measure wound closure, each monkey served as its own control. AdhTERT was used to treat 2 of the wounds on each animal, and Ad-null was administered to the other 2 wounds. Two thirds of each dose was delivered around the wound edge by 8 intra-dermal injections of 5 μL using a Hamilton syringe with a 30 gauge needle. The remaining third of the viral dose was applied topically into the wound defect (20 μL). The percentage of wound area remaining was assessed every other day. Wound tracings were performed using a single-layer plastic film placed over the biopsy site and % wound area remaining was quantified as number of pixels using NIH Image analysis software. Upon complete healing, an 8 mm punch biopsy was collected around each wound and processed for histological and biochemical analysis.

The AdhTERT vector was found to cause hTERT expression in the dermal regions 3 days after wounding and virus administration. FIG. 19 shows the results of the wound healing measurements. Each data point represents the percent wound area remaining averaged for the 2 wound receiving AdhTERT (■) or control vector (●). The effect of transient hTERT expression on wound healing in this model was inconclusive. The adenovirus vector administration did not cause abnormal inflammation, which shows that transient induction of hTERT gene expression in wounds can be done safely.

Example 8

AdhTERT Gene Delivery Promotes Epidermal Migration in Human Skin Tissues

Chronic ulcers are characterized by impaired wound healing and frequently repeated wounding at the same sites. They may be partially due to the compromised regenerative capacity of skin cells as a consequence of replicative senescence. In addition, the aberrant gene expression/phenotype often associated with the state of senescence may further exacerbate the pathology found in chronic wounds.

To extend the other findings provided in this disclosure, an assay of ex-vivo epidermal migration was developed using intact human skin tissues. The tissue was obtained from both normal donors and from donors with chronic wounds, and was used to determine the effect of hTERT gene expression on epidermal migration.

Human skin tissues from autopsy or surgical procedures were provided by Research Tissue Recovery Network (Blue Springs, Mo.) and by Dr. Spencer Brown at University of Texas Southwestern Medical Center (Dallas, Tex.) within 24 hr of isolation. Normal skin tissues were obtained from donors without any wounds or from anatomical sites distal from any affected wounds; wound tissues were obtained from sites close to or at the edges of affected acute or chronic wounds.

Upon receipt, skin tissues were trimmed of subcutaneous fat and washed 5 times using DMEM supplemented with streptomycin (10 µg/mL) and penicillin (10 units/mL). Generally, 4 or 6 mm full thickness punches were made from the skin samples using a sterile biopsy (uni-punch, Premier Medical Products, King of Prussia, Pa.). The skin punches were attached to the bottom of Petri dishes or 6-well tissue culture plates using skin closure glue Nexabond™ (Veterinary Products Laboratories, Phoenix, Ariz.), submerged in DMEM supplemented with 10% FBS and Pen/Strep, and incubated at 37° C. with 5% $CO_2$ for up to 7 days. For each time point, 3 skin punches were harvested and fixed in 10% neutral buffered formalin for 24 h. The tissues were paraffin embedded on edge and 6 micron serial sections were generated. For each skin punch, 3 sections at different depths were stained with H&E and examined under a microscope. Photomicrographs of the sections were taken under a 2.5× object lens and the images saved as JPG files. To cover the entire tissue section, sometimes two overlapping photomicrographs were taken and assembled using Adobe Photo-Shop® software.

FIG. 20 shows H&E sections of normal human skin punches cultured ex vivo. The epidermal layer was distinguished from the dermal region in H&E stained sections due to the difference in cellularity. The epidermal layer migrated along the cut edge of the punches with increasing time in culture. Distance migrated by the epidermal keratinocytes over the cut edge of the dermis was measured on both sides using the NIH Image 1.62 software. The pixel numbers were converted into millimeters by normalizing to the original width of the punches (4 or 6 mm).

FIG. 21 (Top Panel) shows migration of epidermal cells in different media. One was the basic fibroblast medium (DMEM plus 10% FBS) and the other was a 1:1 mixture of fibroblast medium and keratinocyte medium EpiLife™ (Cascade Biologics, Inc., Portland, Oreg.). No significant difference in the distance migrated by the epidermis was observed.

FIG. 21 (Bottom Panel) shows the pattern of epidermal migration for 7 normal human skin tissues over a period of 7 days. 3 skin tissues were of questionable quality due to compromised shipping procedure. Epidermal migration was observed in the other 4 tissues tested. Migration of the epidermis occurred as early as day 1, and plateaued by day 3 or 5. The epidermal layer eventually reached the interface of the dermal and connective tissues and no more migration was observed. The distance migrated in certain samples decreased after 5 days, presumably due to thickening or contraction of the tissues upon long term culture. The epidermal migration rate was relatively consistent among punches obtained from the same donor.

FIG. 22 shows expression of adenoviral delivery of hTERT to human skin punches. AdhTERT was injected into normal (left) or wound derived (right) skin punches from donor GTS 1384. Frozen tissues sections were harvested on day 3 (normal) or day 5 (wound tissue), fixed in 4% paraformaldehyde, and permeabilized in 0.1% Triton X-100™. The sections were blocked in 5% goat serum, incubated with hTERT antibody (1A4, 2.5 µg/mL) for one hour at room temp, and then stained with Texas-Red™ conjugated goat anti-mouse IgG (Jackson Immunolabs).

Upper panels show hTERT staining; lower panels show co-localization with propidium iodide. Administration by injection caused hTERT expression to be mostly localized along the injection path. Bathing with AdhTERT ($10^8$ pfu/mL for 24 h) was less efficient in transducing the dermal cells, although a few cells lining the migrating epidermis did show hTERT expression.

To assess the effect of hTERT on epidermal migration, skin punches were treated with AdhTERT by direct injection or bathing. Results were compared with punches exposed to adenovirus encoding LacZ, adenovirus control (Ad-null), or no virus. One sample of the four tested (GTS 1384, age 78, normal skin) showed significant enhancement (FIG. 23, Top Panel). The epidermis of untreated skin punches or punches treated with AdLacZ stopped migrating by 3 days. In contrast, the punch treated with AdhTERT migrated for 5 days to over twice the distance.

FIG. 23 (Bottom Panel) shows results of normal tissue, and tissue taken from a chronic wound in the same donor (GTS 1388, age 39). Epidermal migration was slower in the wound tissues than the normal tissue, demonstrating impaired healing properties. AdhTERT enhanced migration of the wound tissues by almost 3-fold, but had no effect on the normal tissue.

These results show that hTERT preferentially affects dermal tissues (normal or pathologic) that have sub-optimal epidermal migration. hTERT transduction is not mitogenic, nor does it significantly change the phenotype of young cells. But in older cells, hTERT enables the cells to proliferate further, and causes beneficial ("youthful") changes that result in enhanced migration and epithelializing potential. Even a few hTERT expressing cells can rescue the senescent phenotype and generate growth factors or extracellular matrix components that improve epidermal cell migration over the wound surface.

The compositions and procedures described in this disclosure can be effectively modified by routine optimization without departing from the spirit of the invention embodied in the claims that follow.

Sequence Data

TABLE 4
Sequences Listed in this Disclosure

| SEQ. ID NO: | Descriptive Annotation | Source |
|---|---|---|
| 1 | *Homo sapiens* telomerase reverse transcriptase (TERT) mRNA sequence | GenBank Locus NM 003210. See also Nakamura et al., Science 277:955, 1997; and GenBank Locus AF015950 |
| 2 | *Homo sapiens* telomerase reverse transcriptase (TERT) amino acid sequence | GenBank Locus NM 0032107. |

```
SEQ. ID NO: 1
   1        gcagcgctgc gtcctgctgc gcacgtggga agccctggcc ccggccaccc ccgcgatgcc
  61        gcgcgctccc cgctgccgag ccgtgcgctc cctgctgcgc agccactacc gcgaggtgct
 121        gccgctggcc acgttcgtgc ggcgcctggg gccccagggc tggcggctgg tgcagcgcgg
 181        ggacccggcg gctttccgcg cgctggtggc ccagtgcctg gtgtgcgtgc cctgggacgc
 241        acggccgccc cccgccgccc cctccttccg ccaggtgtcc tgcctgaagg agctggtggc
 301        ccgagtgctg cagaggctgt gcgagcgcgg cgcgaagaac gtgctggcct tcggcttcgc
 361        gctgctggac ggggcccgcg ggggccccccc cgaggccttc accaccagcg tgcgcagcta
 421        cctgcccaac acggtgaccg acgcactgcg ggggagcggg gcgtgggggc tgctgctgcg
 481        ccgcgtgggc gacgacgtgc tggttcacct gctggcacgc tgcgcgctct ttgtgctggt
 541        ggctcccagc tgcgcctacc aggtgtgcgg gccgccgctg taccagctcg gcgctgccac
 601        tcaggcccgg ccccgccac acgctagtgg accccgaagg cgtctgggat gcgaacgggc
 661        ctggaaccat agcgtcaggg aggccgggt cccctgggc ctgccagccc cgggtgcgag
 721        gaggcgcggg ggcagtgcca gccgaagtct gccgttgccc aagaggccca ggcgtggcgc
 781        tgcccctgag ccggagcgga cgcccgttgg gcagggtcc tgggcccacc cggcaggac
 841        gcgtggaccg agtgaccgtg gtttctgtgt ggtgtcacct gccagacccg ccgaagaagc
 901        cacctctttg gagggtgcgc tctctggcac gcgccactcc cacccatccg tgggccgcca
 961        gcaccacgcg ggcccccat ccacatcgcg gccaccacgt ccctgggaca cgccttgtcc
1021        cccggtgtac gccgagacca agcacttcct ctactcctca ggcgacaagg agcagctgcg
1081        gccctccttc ctactcagct ctctgaggcc cagcctgact ggcgctcgga ggctcgtgga
1141        gaccatcttt ctgggttcca ggccctggat gccagggact ccccgcaggt tgccccgcct
1201        gccccagcgc tactggcaaa tgcggcccct gtttctggag ctgcttggga accacgcgca
1261        gtgcccctac ggggtgctcc tcaagacgca ctgcccgctg cgagctgcgg tcaccccagc
1321        agccggtgtc tgtgcccggg agaagcccca gggctctgtg gcggcccccg aggaggagga
1381        cacagacccc cgtcgcctgg tgcagctgct ccgccagcac agcagcccct ggcaggtgta
1441        cggcttcgtg cgggcctgcc tgcgccggct ggtgccccca ggcctctggg gctccaggca
1501        caacgaacgc cgcttcctca ggaacaccaa gaagttcatc tccctgggga agcatgccaa
1561        gctctcgctg caggagctga cgtggaagat gagcgtgcgg gactgcgctt ggctgcgcag
1621        gagcccaggg gttggctgtg ttccggccgc agagcaccgt ctgcgtgagg agatcctggc
```

-continued

```
1681  caagttcctg cactggctga tgagtgtgta cgtcgtcgag ctgctcaggt ctttcttta
1741  tgtcacggag accacgtttc aaaagaacag gctctttttc taccggaaga gtgtctggag
1801  caagttgcaa agcattggaa tcagacagca cttgaagagg gtgcagctgc gggagctgtc
1861  ggaagcagag gtcaggcagc atcgggaagc caggcccgcc ctgctgacgt ccagactccg
1921  cttcatcccc aagcctgacg ggctgcggcc gattgtgaac atggactacg tcgtgggagc
1981  cagaacgttc cgcagagaaa agagggccga gcgtctcacc tcgagggtga aggcactgtt
2041  cagcgtgctc aactacgagc gggcgcggcg ccccggcctc ctgggcgcct ctgtgctggg
2101  cctggacgat atccacaggg cctggcgcac cttcgtgctg cgtgtgcggg cccaggaccc
2161  gccgcctgag ctgtactttg tcaaggtgga tgtgacgggc gcgtacgaca ccatccccca
2221  ggacaggctc acggaggtca tcgccagcat catcaaaccc cagaacacgt actgcgtgcg
2281  tcggtatgcc gtggtccaga aggccgccca tgggcacgtc cgcaaggcct tcaagagcca
2341  cgtctctacc ttgacagacc tccagccgta catgcgacag ttcgtggctc acctgcagga
2401  gaccagcccg ctgagggatg ccgtcgtcat cgagcagagc tcctccctga atgaggccag
2461  cagtggcctc ttcgacgtct tcctacgctt catgtgccac cacgccgtgc gcatcagggg
2521  caagtcctac gtccagtgcc aggggatccc gcaggctcc atcctctcca cgctgctctg
2581  cagcctgtgc tacgcgacga tggagaacaa gctgtttgcg gggattcggc gggacgggct
2641  gctcctgcgt ttggtggatg atttcttgtt ggtgacacct cacctcaccc acgcgaaaac
2701  cttcctcagg accctggtcc gaggtgtccc tgagtatggc tgcgtggtga acttgcggaa
2761  gacagtggtg aacttccctg tagaagacga ggccctgggt ggcacggctt tgttcagat
2821  gccggcccac ggcctattcc cctggtgcgg cctgctgctg atacccggga ccctggaggt
2881  gcagagcgac tactccagct atgcccggac ctccatcaga gccagtctca ccttcaaccg
2941  cggcttcaag gctgggagga acatgcgtcg caaactcttt ggggtcttgc ggctgaagtg
3001  tcacagcctg tttctggatt tgcaggtgaa cagcctccag acggtgtgca ccaacatcta
3061  caagatcctc ctgctgcagg cgtacaggtt tcacgcatgt gtgctgcagc tcccatttca
3121  tcagcaagtt tggaagaacc ccacattttt cctgcgcgtc atctctgaca cggcctccct
3181  ctgctactcc atcctgaaag ccaagaacgc agggatgtcg ctgggggcca agggcgccgc
3241  cggccctctg ccctccgagg ccgtgcagtg gctgtgccac caagcattcc tgctcaagct
3301  gactcgacac cgtgtcacct acgtgccact cctgggtca ctcaggacag cccagacgca
3361  gctgagtcgg aagctcccgg ggacgacgct gactgccctg gaggccgcag ccaacccggc
3421  actgccctca gacttcaaga ccatcctgga ctgatggcca cccgcccaca gccaggccga
3481  gagcagacac cagcagccct gtcacgccgg gctctacgtc cagggaggg aggggcggcc
3541  cacacccagg cccgcaccgc tgggagtctg aggcctgagt gagtgtttgg ccgaggcctg
3601  catgtccggc tgaaggctga gtgtccggct gaggcctgag cgagtgtcca gccaagggct
3661  gagtgtccag cacacctgcc gtcttcactt cccacaggc tggcgctcgg ctccacccca
3721  gggccagctt tcctcacca ggagcccggc ttccactccc cacataggaa tagtccatcc
3781  ccagattcgc cattgttcac ccctcgccct gccctccttt gccttccacc cccaccatcc
3841  aggtggagac cctgagaagg accctgggag ctctgggaat ttggagtgac caaggtgtg
3901  ccctgtacac aggcgaggac cctgcacctg gatgggggtc cctgtgggtc aaattggggg
3961  gaggtgctgt gggagtaaaa tactgaatat atgagttttt cagttttgaa aaaaa
```

SEQ. ID NO: 2
MPRAPRCRAVRSLLRSHYREVLPLATFVRRLGPQGWRLVQRGDP

-continued

AAFRALVAQCLVCVPWDARPPPAAPSFRQVSCLKELVARVLQRLCERGAKNVLAFGFA

LLDGARGGPPEAFTTSVRSYLPNTVTDALRGSGAWGLLLRRVGDDVLVHLLARCALFV

LVAPSCAYQVCGPPLYQLGAATQARPPPHASGPRRRLGCERAWNHSVREAGVPLGLPA

PGARRRGGSASRSLPLPKRPRRGAAPEPERTPVGQGSWAHPGRTRGPSDRGFCVVSPA

RPAEEATSLEGALSGTRHSHPSVGRQHHAGPPSTSRPPRPWDTPCPPVYAETKHFLYS

SGDKEQLRPSFLLSSLRPSLTGARRLVETIFLGSRPWMPGTPRRLPRLPQRYWQMRPL

FLELLGNHAQCPYGVLLKTHCPLRAAVTPAAGVCAREKPQGSVAAPEEEDTDPRRLVQ

LLRQHSSPWQVYGFVRACLRRLVPPGLWGSRHNERRFLRNTKKFISLGKHAKLSLQEL

TWKMSVRDCAWLRRSPGVGCVPAAEHRLREEILAKFLHWLMSVYVVELLRSFFYVTET

TFQKNRLFFYRKSVWSKLQSIGIRQHLKRVQLRELSEAEVRQHREARPALLTSRLRFI

PKPDGLRPIVNMDYVVGARTFRREKRAERLTSRVKALFSVLNYERARRPGLLGASVLG

LDDIHRAWRTFVLRVRAQDPPPELYFVKVDVTGAYDTIPQDRLTEVIASIIKPQNTYC

VRRYAVVQKAAHGHVRKAFKSHVSTLTDLQPYMRQFVAHLQETSPLRDAVVIEQSSSL

NEASSGLFDVFLRFMCHHAVRIRGKSYVQCQGIPQGSILSTLLCSLCYGDMENKLFAG

IRRDGLLLRLVDDFLLVTPHLTHAKTFLRTLVRGVPEYGCVVNLRKTVVNFPVEDEAL

GGTAFVQMPAHGLFPWCGLLLDTRTLEVQSDYSSYARTSIRASLTFNRGFKAGRNMRR

KLFGVLRLKCHSLFLDLQVNSLQTVCTNIYKILLLQAYRFHACVLQLPFHQQVWKNPT

FFLRVISDTASLCYSILKAKNAGMSLGAKGAAGPLPSEAVQWLCHQAFLLKLTRHRVT

YVPLLGSLRTAQTQLSRKLPGTTLTALEAAANPALPSDFKTILD

---

What is claimed as the invention is:

1. A method for accelerating the healing of an epithelial wound, comprising administering to the wound site a composition that contains epithelial cells that have been transfected with a nucleic acid vector that encodes and expresses telomerase reverse transcriptase (TERT).

2. The method of claim 1, wherein the composition further comprises fibroblasts.

3. The method of claim 2 wherein the fibroblasts in the composition have also been transfected with a vector that encodes and expresses telomerase reverse transcriptase (TERT).

4. The method of claim 1, wherein the epithelial cells migrate on a solid surface at a rate of at least two cell diameters per day.

5. The method of claim 1, wherein the wound is a skin wound.

6. The method of claim 1, wherein the composition further comprises a means for retaining the epithelial cells at or around the wound site.

7. The method of claim 1, further comprising monitoring the wound for closure.

8. The method of claim 1, wherein the epithelial cells have been transduced with an adenovirus expression vector that encodes and expresses telomerase reverse transcriptase (TERT).

9. The method of claim 1, wherein the epithelial cells express at least 2 TPG units of telomerase activity as measured in a telomeric repeat amplification protocol (TRAP) assay.

10. A method for accelerating the healing of a wound to the skin, comprising administering to the wound site a composition that contains keratinocytes that have been transfected with a nucleic acid vector that encodes and expresses telomerase reverse transcriptase (TERT).

11. The method of claim 10, wherein the composition further comprises fibroblasts.

12. The method of claim 11, wherein the fibroblasts in the composition have also been transfected with a nucleic acid vector that encodes and expresses telomerase reverse transcriptase (TERT).

13. The method of claim 10, wherein the epithelial cells migrate on a solid surface at a rate of at least two cell diameters per day.

14. The method of claim 10, wherein the composition further comprises a means for retaining the epithelial cells at or around the wound site.

15. The method of claim 10, further comprising monitoring the wound for closure.

16. The method of claim 1 or claim 10, wherein the teolmerase reverse transcriptase (TERT) is human telomerase reverse transcriptase (hTERT).

* * * * *